(12) United States Patent
Carreira et al.

(10) Patent No.: US 10,421,792 B2
(45) Date of Patent: *Sep. 24, 2019

(54) ANTIMICROBIAL PROTEIN

(75) Inventors: Alexandra Manuela Lourenço Carreira, Cantanhede (PT); Ricardo Manuel De Seixas Boavida Ferreira, Cantanhede (PT); Sara Alexandra Valadas Da Silva Monteiro, Cantanhede (PT)

(73) Assignee: CONSUMO EM VERDE BIO TECHNOLOGIA DAS PLANTAS, S.A., Cantanhede (PT)

( * ) Notice: Subject to any disclaimer, the term of this patent is extended or adjusted under 35 U.S.C. 154(b) by 163 days.

This patent is subject to a terminal disclaimer.

(21) Appl. No.: 13/879,151

(22) PCT Filed: Oct. 12, 2011

(86) PCT No.: PCT/EP2011/067824
§ 371 (c)(1),
(2), (4) Date: Oct. 14, 2015

(87) PCT Pub. No.: WO2012/049215
PCT Pub. Date: Apr. 19, 2012

(65) Prior Publication Data
US 2016/0052978 A1 Feb. 25, 2016

(30) Foreign Application Priority Data

Oct. 12, 2010 (PT) .......................................... 105330
Oct. 13, 2010 (GB) .................................. 1017284.9

(51) Int. Cl.
C07K 14/415 (2006.01)
A23L 3/3463 (2006.01)
A61K 38/16 (2006.01)
A01N 47/40 (2006.01)
A61K 36/48 (2006.01)

(52) U.S. Cl.
CPC ............ *C07K 14/415* (2013.01); *A01N 47/40* (2013.01); *A23L 3/34635* (2013.01); *A61K 38/168* (2013.01); *A23V 2002/00* (2013.01); *A61K 36/48* (2013.01); *Y02A 50/481* (2018.01)

(58) Field of Classification Search
None
See application file for complete search history.

(56) References Cited

U.S. PATENT DOCUMENTS

| 7,067,624 | B2 | 6/2006 | Manners |
| 9,095,166 | B2* | 8/2015 | Valadas Da Silva Monteiro ........ A21D 2/267 |
| 9,402,404 | B2* | 8/2016 | Carreira ................. A21D 2/267 |
| 2004/0101580 | A1 | 5/2004 | Msika |
| 2004/0138176 | A1* | 7/2004 | Miles ............... 514/65 |
| 2007/0258996 | A1 | 11/2007 | Sterilex |
| 2008/0300137 | A1* | 12/2008 | De Seixas Boavida Ferreira et al. ............................ 504/189 |
| 2016/0052978 | A1* | 2/2016 | Carreira .............. A23L 3/34635 514/2.7 |

FOREIGN PATENT DOCUMENTS

| EP | 1 559 417 A | 8/2005 |
| JP | 2004 131500 | 4/2004 |
| WO | WO 93/11783 | * 6/1993 |
| WO | WO93/11783 | 6/1993 |
| WO | WO98/47479 | 10/1998 |
| WO | WO2004-071521 | 8/2004 |
| WO | WO 2005/1022559 | 11/2005 |
| WO | WO2006/003110 | 1/2006 |
| WO | WO2007/010459 | 1/2007 |
| WO | WO2007/122421 | 11/2007 |

OTHER PUBLICATIONS

John M Wells et al: "In vitro Inhibition of Soft-Rotting Bacteria by EDTA and Nisin and in vivo Response on Inoculated Fresh Cut Carrots", Plant Disease, Jan. 1, 1998 (Jan. 1, 1998 ), pp. 491-495, XP55014413, Retrieved from the Internet: U RL:http://apsjournals. apsnet.org/doi/pdf/10.1094/PDIS.1998.82.5.491 [retrieved on Dec. 9, 2011].*

Arun K Chatterjee et al: "Unusual Susceptibility of Erwinia amylovora to Antibacterial Agents in Relation to the Barrier Function of its Cell Envelope", Antimicrobial Agents and Chemotherapy, May 1, 1977 (May 1, 1977 ), pp. 897-905, XP55014414, Retrieved from the Internet: U RL:http://www.ncbi.nlm.nih.gov/pmc/articles/PMC352093/pdf/aac00299-0135.*

Haque H et al: "Cell Envelopes of Gram Negative Bacteria: Composition, Response to Chelating Agents and Susceptibility of Whole Cells to Antibacterial Agents", Journal of Applied Bacteriology, Blackwell Publishing Ltd., Oxford, GB, vol. 40, No. 1,Jan. 1, 1976 (Jan. 1, 19756 ), pp. 89-99, XP009048176, ISSN: 0021-8847.*

(Continued)

Primary Examiner — Maury A Audet
(74) Attorney, Agent, or Firm — Adam Warwick Bell; Matthew Rupert Kaser

(57) ABSTRACT

The inventors provide a composition comprising an antimicrobial polypeptide comprising Blad or an active variant thereof for use in a method of treatment of the human or animal body by therapy or prophylaxis, such as for use in a method of treating or preventing an infection in or on a subject by a microorganism. Also provided is the use of a composition comprising an antimicrobial polypeptide comprising Blad or an active variant thereof to kill, or inhibit the growth of, a microorganism that is pathogenic to a human or an animal at a site that is not on or in the human or animal body.

9 Claims, 10 Drawing Sheets
Specification includes a Sequence Listing.

(56) References Cited

OTHER PUBLICATIONS

Peumans et al. "Lectins as Plant Defense Proteins", Plant Physiology, Jan. 1, 1995 (Jan. 1, 1995), pp. 347-352, XP55014530, Retrieved from the Internet: URL:. gov/pmc/articles/PMCI 57596/pdf/1090347.pdf [retrieved on Dec. 12, 2011].*
Oliveira et al. "Purification of a lectin from *Eugenia uniflora* L. seeds and its potential antibacterial activity", Letters in Applied Microbiology, vol. 46, No. 3, Mar. 1, 2008 (Mar. 1, 2008), pp. 371-376, XP55014526, ISSN: 0266-8254, DOI: 10.1111/j.1472-765X. 2007.02319.x.*
Hayat. Why is it More Difficult to Treat Gram Negative Bacteria. Medimoon. 2013. http://medimoon.com/2013/04/why-is-it-more-difficult-to-treat-gram-negative-bacteria/.*
Oliveria et al, *Purification of a lectin from Eugenia uniflora L. seeds and its potential activity* Lett. Appl. Microbiol. 46; 2008, p. 371-376.
PLoS One 5 (Mar. 23, 2010) Monterio et al *The Unique biosynthetic route from lupinus beta-conglutin gene to blad*; ISSN1932-6203.
Ribeiro, Ana Cristina Ferreira da Concicao, 2009, Thesis: "*Analise Molecular . . .* " 2009; XP002666464.
Robin Wait et al, *Analysis of Lupinus albus Storage Proteins by Two-Dimensional Electrophoresis . . .* ; J. Agricult. and Food Chem. vol. 53 No. 11; Jun. 1, 2005.
Woldemicheal G M et al, *Triterpene glycosides of Lupinus angustifolius*; Phytochemistry, Pergamon Press, GB vol. 60, No. 4, Jun. 1, 2002.
Hancock et al., Cationic peptides: *A new source of antibiotics.* Trends in Biotechnology, TIBTECH Feb. 1998 vol. 16 pp. 82-88.
Jouandeaud *The influence of oligisacharides on skin aging . . .* Cosmetics & Toiletries; Wheaton IL vol. 119 No. 6 Jun. 1, 2004.

* cited by examiner

```
   1 gatggcgatg aatgaacact gcgtttgctg gctttgatga aaatcgagtg caacctaata
  61 taatcaaata tgggtaagat gagagtgagg tttccaacgt tagtgtttgt actaggaata
 121 gtattcctca tggcagtgtc aattgtatt gcttatggag aaaaagatgt gctaaagagt
 181 catgagaggc ctgaggaaag agaacaagag gagtgcaac ctaggagaca acgacctcaa
 241 agtagaaggg aagagagaga gcaagacaa gagcagggtt ctccctcata cccacgcagg
 301 cagagtggtt atgagaggag acaataccat gagaggagtg agcagaggga agagagagag
 361 caagaacaac aacaaggttc tccctcatac tcacgtagac aaaggaaccc ttatcacttc
 421 agctctcaaa gattccaaac tctttacaaa aataggaatg gcaaaatccg tgtgctcgag
 481 aggtttgacc aaagaaccaa tagacttgag aatctccaaa actaccgcat tgttgagttc
 541 caatcaaaac ctaacactct cattctccct aaacactctg atgctgacta cgtcctcgtt
 601 gtactcaatg gtagagccac aatcacgata gtaaaccctg ataagaaca agcatataac
 661 cttgagtatg gcgatgctct cagaatccca gctggctcaa cttcatatat ccttaacccg
 721 gatgacaacc agaagcttag agtagtcaag ctcgcaatac ccatcaacaa tcctggctac
 781 ttttatgatt tctatccatc gagtactaaa gaccaacaat cctacttcag tggcttcagc
 841 aggaacactt tagaggccac cttcaatact cgttatgaag agatacaaag gattattta
 901 gggaatgagg atgagcaaga atatgaggaa caaggcgtg ggcaagagca gagcgaccaa
 961 gacgaggggg tgatagtgat agtttcaaag aaacagatcc aaaaattgac aaaacacgct
1021 caatcttcat caggaaaaga caaccctct gattctggcc ccttcaactt gagaagcaat
1081 gagcccatat attcaaacaa gtatgggaac ttctatgaaa tcactccaga tagaaaccct
1141 caagttcagg atttgaatat ctctctcacc tatataaaaa ttaacgaggg agcttgttg
1201 ttgccacact ataactcaaa ggccatatat gtagtcgtgg ttgatgaagg agaaggaaat
1261 tatgaactgg taggtattcg agatcaacaa cgacaacaag atgagcaaga agagagagag
1321 gaagaagtga taaggtatag tgctagatta tcagaaggtg acattttgt aattccagca
1381 ggttatccaa tttccatcaa tgcttcctca aatcttcgct tgcttggatt tggcatcaat
1441 gctgatgaaa accagaggaa tttcctcgca ggttctaaag acaatgtgat aaggcagtta
1501 gatagagcag tgaatgagct cacattccct ggttctgctg aagatattga gagattaatc
1561 aaaaaccaac aacagtctta ctttgcaaat ggtcagcctc aacaacaaca acaacaacaa
1621 agtgagaagg agggaaggcg tggaagaagg ggttcatctc ttccatttg agcactttt
1681 actaagctgt tttaaaagct actatcatgt aagagctcat agtgagctac tgagagaata
1741 ataaaactaa agttggacct ttgtactaat aatgttaata aaaaaaaaa a
```

Figure 11

```
  1 cgtagacaaa ggaaccctta tcacttcagc tctccaaagat tccaaactct ttacaaaaat
 61 aggaatggca aaatccgtgt gctcgagagg tttgaccaaa gaaccaatag acttgagaat
121 ctccaaaact accgcattgt tgagttccaa tcaaaaccta acactctcat tctccctaaa
181 cactctgatg ctgactacgt cctcgttgta ctcaatggta gagccacaat cacgatagta
241 aaccctgata gaagacaagc atataacctt gagtatggcg atgctctcag aatcccagct
301 ggctcaactt catatatcct taacccggat gacaaccaga agcttagagt agtcaagctc
361 gcaataccca tcaacaatcc tggctacttt tatgatttct atccatcgag tactaaagac
421 caacaatcct acttcagtgg cttcagcagg aacactttag aggccacctt caatactcgt
481 tatgaagaga tacaaaggat tattttaggg aatgaggat
```

ANTIMICROBIAL PROTEIN

The present US national phase application claims priority to and the benefit of the following, to the extent allowable by law: PCT/EP2011/067824 (WO/2012/049215) filed 12 Oct. 2011 and priority applications PT 105330 filed 12 Oct. 2010 and GB 1017284.9 filed 13 Oct. 2010, all of which, together with all references disclosed in this and all priority applications, are hereby incorporated by reference for all purposes.

A sequence listing text (.txt) file is submitted herewith under 37 CFR. 1.821(c) and is transferred from PCT/EP2011/067824 under 37 CFR 1.821(e), and is hereby incorporated by reference in its entirely. The details of the file as required under See 37 CFR. 1.52(e)(5) and 37 CFR 1.77(b)(5) are as follows: Name of file is P11335_WO_ST25.txt; date of creation is 12 Apr. 2013; size is 10,000 bytes. The information recorded in electronic form (if any) submitted (under Rule 13ter if appropriate) with this application is identical to the sequence listing as contained in the application as filed.

FIELD OF THE INVENTION

The invention relates to the field of antimicrobial agents, and especially those that target human/animal pathogens.

INTRODUCTION

Bacterial Infections

Bacteria are, by far, the most common aetiological agents of human infection. More than one-third of the world population is likely infected by bacterial pathogens, and two million fatalities occur per year from bacterial infections. According to the Centre for Disease Control (CDC) and the World Health Organization (WHO), the following bacterial infections are included in the list of the most common infectious diseases throughout the world today:

Cholera: this is a disease spread mostly through contaminated drinking water and unsanitary conditions. It is endemic in the Indian subcontinent, Russia, and sub-Saharan Africa. It is an acute infection of the intestine with the bacterium *Vibrio cholerae*. The main symptom is copious diarrhoea. Between 5% and 10% of those infected with the disease will develop severe symptoms, which include vomiting and leg cramps. In its severe form, cholera can cause death by dehydration. An estimated 200,000 cases are reported to the WHO annually.

Meningitis: often known as spinal meningitis, this is an infection of the spinal cord. It is usually the result of a viral or bacterial infection. Bacterial meningitis is more severe than viral meningitis and may cause brain damage, hearing loss, and learning disabilities. It may be caused by, for example, *Haemophilus influenzae* type b, *Neisseria meningitidis*, or *Streptococcus pneumoniae*. An estimated 1.2 million cases of bacterial meningitis occur every year, over a tenth of which are fatal. Symptoms include severe headache, fever, nausea, vomiting, lethargy, delirium, photophobia, and a stiff neck.

Pneumonia: this has many possible causes, but it is usually an infection of *Streptococcus* or *Mycoplasma* bacteria. These bacteria can live in the human body without causing infection for years, and only surface when another illness has lowered the immunity to disease. *Streptococcus pneumoniae* causes streptococcal pneumonia, the most common kind, which is more severe than mycoplasmal pneumonia. *S. pneumoniae* is responsible for more than 100,000 hospitalizations for pneumonia annually, as well as 6 million cases of otitis media and over 60,000 cases of invasive diseases such as meningitis.

Shigellosis: this infection causes an estimated 600,000 deaths worldwide every year. It is most common in developing countries with poor sanitation. *Shigella* bacteria cause bacillary dysentery, or shigellosis. Symptoms include diarrhea with bloody stool, vomiting, and abdominal cramps.

Strep Throat: this is caused by *Streptococcus* bacteria. Several million cases of strep throat occur every year. Symptoms include a sore throat, fever, headache, fatigue, and nausea.

Tuberculosis: this causes nearly 2 million deaths every year, and WHO estimates that nearly 1 billion people will be infected between 2000 and 2020 if more effective preventive procedures are not adopted. The TB bacteria (e.g. *Mycobacterium tuberculosis*) are most often found in the lungs, where they can cause chest pain and a bad cough that brings up bloody phlegm. Other symptoms include fatigue, weight loss, appetite loss, chills, fever, and night sweats.

Typhoid: typhoid fever is caused by the bacterium *Salmonella typhi*, and causes an estimated 600,000 deaths annually, out of 12-17 million cases. It is usually spread through infected food or water. Symptoms include a sudden and sustained fever, severe headache, nausea, severe appetite loss, constipation, and sometimes diarrhoea.

Accurate caseload numbers are, however, difficult to determine, especially because so many of these diseases are endemic to developing countries, where many people do not have access to modern medical care. Approximately half of all deaths caused by infectious diseases each year can be attributed to just three diseases: tuberculosis, malaria, and AIDS. Together, these diseases cause over 300 million illnesses and more than 5 million deaths each year.

The modern era of antibiotic use began in the nineteenth and early twentieth centuries, with the identification of the active ingredient penicillin, produced by *Penicillium notatum*, which had potent antimicrobial activity. However, prior to 1955, its sale was not controlled and excessive and uncontrolled use led to the emergence of resistant bacteria. Antibiotic resistance became a major problem, and epidemics of staphylococcal-resistant infections began to emerge in hospitals.

The early twentieth century also saw the development of antibiotics such as sulfonamides, streptomycin, neomycin, chloramphenicol, cephalosporins and tetracyclines. Many of these compounds are still in use today though all have faced the challenge of the development of resistance and some have faced toxicity issues. For example, streptomycin can cause kidney damage and deafness and chloramphenicol may cause serious side effects (e.g. serious blood disorders, including anemia and leukemia).

Further research took place during the 1960s, which led to the development of the second generation of antibiotics. Among these was methicillin, a semi-synthetic derivative of penicillin produced specifically to overcome the problem of penicillin resistance. Methicillin was hailed as a major breakthrough in the fight against bacterial resistance to penicillin, but, unfortunately, that was not the case, and there are now bacteria that are resistant to methicillin. Ampicillin is also a derivative of penicillin. It was developed to broaden the range of infections that penicillin could treat and has now replaced penicillin to a great extent. It is often the first choice in the treatment of a whole range of infections, including respiratory and urinary tract infections. Amoxicillin is another widely used penicillin derivative. Like ampicillin, it has a broad range of activities. Gentamicin is in the same family of antibiotics as streptomycin (the anti-TB drug discovered in 1943). It is generally reserved for serious infections, as it can have severe toxic side effects on the ears and kidneys.

Recently, a new family of antibiotics called quinolones, also referred to as fluoroquinolones, has been developed by pharmaceutical laboratories. In addition to being effective against a broad range of bacteria, these antibiotics can reach a high concentration in the bloodstream when taken orally. This means that many more infections that may once have required a hospital stay may now be treated at home. The fluoroquinolones are only used for patients that are seriously ill and/or when long courses of antibiotics (weeks to months) are required.

Despite the development of such second generation compounds, the unceasing emergence of resistance continues to be a problem. Typically, resistance follows use, and especially widespread use or misuse of a drug, which will eventually lead to its loss of effectiveness for treating human illness. The continuous use of antimicrobial agents increases selection pressure favouring the emergence, multiplication, and spread of resistant strains. Inappropriate and uncontrolled use of antimicrobial agents contribute to this, including overprescribing, administration of suboptimal doses, insufficient duration of treatments, misdiagnosis leading to inappropriate choice of drug, and the use (and, specifically, overuse) of antibacterial household products in homes, schools etc.

In some cases, resistance appears quickly (e.g. resistance of *Staphylococcus aureus* to oxalin was developed in just a few years), but in others it may take longer (e.g. *Enterococcus faecium* took almost 30 years to develop resistance to vancomycin). The reasons for the differences in time frames are unclear and probably multifactorial. However, the ability of bacteria to circumvent the killing action of antimicrobial agents has clearly impeded the ability to treat individual patients and to control large outbreaks of infectious diseases. For example, the WHO estimates that there are nearly half a million new cases of multidrug-resistance tuberculosis (MDR-TB) a year, which is about 5% of nine million new TB cases of all types.

Some strains of methicillin-resistant *Staphylococcus aureus* (MRSA) have a particular facility for nosocomial transmission. In some hospitals in the USA, over 70% of the *S. aureus* isolated from patients are MRSA, and these strains often are resistant to all licensed drugs except vancomycin, linezolid, daptomycin, and tigecycline. Recently, strains of *S. aureus* completely resistant to vancomycin were also isolated from patients in the United States further complicating therapy. MRSA has become highly endemic in many hospitals, and once introduced into a hospital, this organism is very difficult to eradicate.

Problems with eradication are also true for vancomycin-resistant strains of *E. faecium* (VRE), which are often resistant to all other clinically approved drugs. Vancomycin resistance in enterococci is often plasmid mediated and may result from several unique resistance determinants. The combination of penicillin and glycopeptide resistance in *E. faecium* causes infections which cannot be effectively treated. Fortunately, most VRE cause colonization and not infection. When infection does occur, it may not be treatable with antibiotics. Resistance to quinolones can evolve rapidly, even during the course of a treatment.

Presently, some bacteria have achieved the status of "superbugs", like methicillin-resistant *Staphylococcus aureus*, vancomycin-resistant enterococci, and quinolone-resistant *Streptococcus pneumonia*. For these pathogens there are few or no antibiotics available for therapy. But, surprisingly, only a few classes of novel antibiotics have been introduced in the past 40 years, and all since 1999, including the streptogramin combination quinupristin/dalfopristin (Synercid), the oxazolidinone linezolid, and the lipopeptide daptomycin.

There is a growing need for novel antibiotics to treat diseases induced by bacterial pathogens, particularly because of the antimicrobial resistance issue. As previously mentioned, many pathogens are developing resistance to potent antibiotics used for treatment. Alarmingly, resistance is often not restricted to a single agent but may involve resistance to multiple antibiotics. The search for new and more effective drugs continues today, especially for directed-spectrum antibiotics to circumvent multidrug-resistance mechanisms. The pace of this search, however, has slowed remarkably, as it is now much more difficult for pharmaceutical companies to get approval for new drugs. In addition, the cost involved and the time delay between the identification of a novel antibiotic in the laboratory and the approval to produce it commercially are so great that it has led some companies to abandon the marketplace completely.

Fungal Infections

The incidence of fungal infections has increased in the last three decades as a consequence, in part, of the increased number of patients having a dysfunctional immune system. This is a direct result of major advances in medicine in recent years, particularly in cancer therapy, resulting in an increased number of immunosuppressed patients. Several other reasons have been proposed for the increase of fungal infections, including parenteral nutrition and central venous catheters, broad-spectrum antibiotic treatment, pregnancy, patients with uncontrolled diabetes, solid organ transplant recipients, patients with AIDS, cancer patients undergoing cytotoxic chemotherapy, patients with burns or neutropenia, and gastrointestinal pathologies.

The most serious of fungal infections are the invasive fungal infections (IFIs) (e.g. bloodstream infection) which are associated with high mortality. *Candida* species are the most frequent causative agents of IFIs with an average mortality rate of 30%. *Candida albicans* is responsible for about 50% of cases of invasive *Candida* infection, but there has been a steady increase in the relative frequencies of non-*albicans* species of *Candida*, namely of *Candida glabrata*, *Candida parapsilosis*, *Candida tropicalis* and *Candida krusei*. *Aspergillus* species are the most commonly isolated invasive moulds, with a predominance of the species *Aspergillus fumigatus*. Like *Candida* infections, invasive aspergillosis is usually associated with critically ill patients, but its mortality rate is much higher, albeit dependent upon the specific individual infection considered: e.g. 85% or more for disseminated or central nervous system disease, and 60% for diffuse pulmonary disease.

The prevalence and mortality rate of IFIs have increased over the past three decades. US data show that in 1980 this group of diseases was responsible for 828 deaths and was the 10th most prominent cause of fatal infection. In 1997, the same data set showed that the number of deaths had risen to 2370 and to the seventh most prevalent cause of terminal infection. Recent data show that *Candida* has become more prevalent than *Escherichia coli* and *Pseudomonas* species and is now the fourth most common fatal infection in the USA.

*Candida* IFIs are also increasing in the nosocomial setting, and a further increment is foreseen as the risk factors of these infections will continue to increase. *Candida* species account for 8 to 10% of all nosocomial IFIs and occur at a rate of 6 to 23 infections for 100,000 persons annually in the USA. The major concern with invasive candidiasis is not only its high mortality rate, but also the excessive length of hospital stay for infected patients, from 3 to 10 days, giving an overall estimated cost attributable to candidemia of about 1 billion dollars per year in the USA. A study recently published on the Portuguese population showed that there is an incidence of nosocomial fungemia of 2.7 per 1,000 hospital admissions, with a mortality rate of 39.3%. According to another recent study published on the incidence of IFIs in Europe, this number seems to be closer to the incidences found in other European countries, but is considerably lower than that found for the USA population. Another recent report showed that in Scotland the incidence of candidemia is 4.8 cases per 100,000 population per year.

Since the late 1950s, the standard of care for treatment of life threatening fungal infection had been amphotericin B. This compound targets and binds to sterols in the fungal cell membrane to create ionic pores, resulting in loss of membrane potential and subsequent collapse. Although it remains the broadest-spectrum fungicidal agent available, its high toxicity and requirement for parenteral administration has limited its use.

The 1990s saw the introductions of lipid formulations of amphotericin B, as well as the triazoles, fluconazole and itraconazole. Triazoles act by affecting the synthesis of ergosterol through the inhibition of CYP-450-dependent lanosterol 14α-demethylase, which interferes with cell growth, eventually leading to cell death. Although these agents exhibited clear advantages over amphotericin B, they were limited by formulation, spectrum of activity and/or development of resistance.

Since 2000, new antifungal agents have been developed to overcome the strong limitations of the pre-existing drugs, such as extended-spectrum triazoles (voriconazole and posaconazole), and echinocandins (caspofungin, micafungin and anidulafungin). Echinocandins inhibit the synthesis of β-1, 3-D-glucans, leading to destabilization of the fungal cell wall, cell lysis, and cell death. They are active, in vitro, against *Candida* and *Aspergillus* species, but not against a wide range of other emergent pathogenic fungi. Even among these new agents, there are still limitations like adverse drug effects (especially for voriconazole), drug-drug interactions associated with triazoles, and lack of alternative preparations (e.g. intravenous preparations are lacking for posaconazole and oral preparations are lacking for echinocandins).

Antifungals now available are also inefficient for the prophylactic eradication of *Candida albicans* colonization. Indeed, this yeast exhibits the capacity for biofilm growth, which displays increased intrinsic tolerance to antifungals such as azoles, polyenes and 5-fluorocytosine. For this reason, candidiasis is often associated with indwelling medical devices (e.g., dental implants, catheters, heart valves, vascular bypass grafts, ocular lenses, artificial joints, and central nervous system shunts), which can act as substrates for biofilm growth. In a multicenter study of 427 consecutive patients with candidemia, the mortality rate for patients with catheter-related candidemia was found to be 41%. Therefore, despite the development of new antifungals, the mortality rate of nosocomial fungal infection remains unacceptably high. Furthermore, there is also a growing list of new and emerging fungal pathogens, including non-albican species of *Candida* and non-*fumigatus* species of *Aspergillus*, which are generally more difficult to diagnose and treat, making them responsible for higher rates of mortality.

It is among the objectives of the present invention to attempt a solution to these problems, and specifically for example to provide an alternative antimicrobial agent with potent and broad-spectrum activity against human/animal pathogens whilst having low toxicity.

SUMMARY OF THE INVENTION

The inventors have surprisingly found that the Blad polypeptide from *Lupinus* shows potent antimicrobial activity against a large number of diverse bacterial and fungal organisms that are pathogenic to humans or animals. The inventors have also found that the Blad polypeptide is non-toxic to animals, therefore making Blad an excellent compound for use as an antimicrobial against human and animal pathogens in a range of settings.

Accordingly, the inventors provide a composition comprising an antimicrobial polypeptide comprising Blad or an active variant thereof for use in a method of treatment of the human or animal body by therapy or prophylaxis. The inventors also provide said composition for use in a method of treating or preventing an infection in or on a subject by a microorganism. In preferred embodiments the composition further comprises a pharmaceutically acceptable carrier or diluent and/or a chelating agent. Preferably the composition is used in said method wherein the subject has a compromised immune system or is critically ill.

The inventors also provide the use of a composition comprising an antimicrobial polypeptide comprising Blad or an active variant thereof to kill, or inhibit the growth of, a microorganism that is pathogenic to a human or an animal at a site that is not on or in the human or animal body. Preferably, said composition is used to disinfect, with respect to a human or animal pathogenic microorganism, an article that is to be ingested by, or placed directly on or in, a human or animal, or a surface that is in need thereof, preferably wherein said article is a foodstuff or a medical device or instrument or wherein said surface is located within an environment where:
  (a) medical examination, diagnosis or treatment is to take place;
  (b) a foodstuff is to be prepared or otherwise handled or stored;
  (c) personal washing and/or sanitation is to take place; and/or
  (d) a person at particular risk of
    (i) acquiring an infection by a microorganism; and/or
    (ii) being unable to clear a microbial infection without medical intervention; is situated.

In preferred embodiments of these uses said composition further comprises a chelating agent.

In preferred embodiments the microorganism is a bacterium or a fungus, preferably wherein:
  the bacterium is a pathogenic species from one of the following genera: *Pseudomonas, Listeria, Bacillus, Staphylococcus* and *Salmonella*; or
  the fungus is a pathogenic species from one of the following genera: *Candida, Aspergillus, Alternaria, Fusarium, Cryptococcus* and *Trichosporon*, preferably wherein the fungus can cause invasive fungal infection, preferably *C. albicans, A. fumigatus* or *Alternaria alternata*.

The inventors also provide:
  a method of treating a human or animal comprising administering to a subject in need thereof a composition comprising a therapeutically effective amount of an antimicrobial polypeptide comprising Blad or an active variant thereof;

a method of preventing or treating an infection by a microorganism comprising administering to a subject in need thereof a composition comprising a therapeutically effective amount of an antimicrobial polypeptide comprising Blad or an active variant thereof; and a method of killing, or inhibiting the growth of, a microorganism that is pathogenic to a human or an animal at a site that is not on or in the human or animal body, said method comprising administering to said site a composition comprising an effective amount of an antimicrobial polypeptide comprising Blad or an active variant thereof.

BRIEF DESCRIPTION OF THE DRAWINGS

The invention will be described with reference to the accompanying drawings, in which:

FIG. 10 shows the *Lupinus albus* β-conglutin precursor encoding sequence (SEQ ID NO: 1); and FIG. 11 shows the internal fragment of the β-conglutin precursor encoding sequence that corresponds to Blad (SEQ ID NO: 3).

DETAILED DESCRIPTION OF THE INVENTION

Blad

Figure 1:
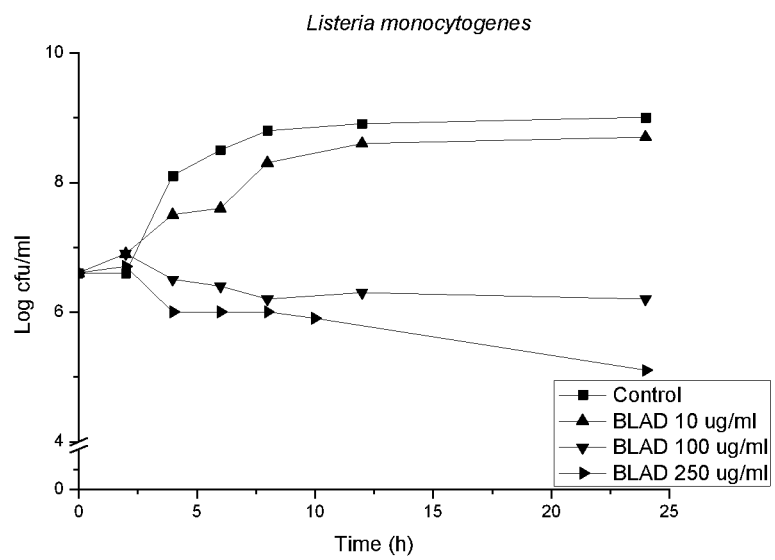
FIG. 1 shows time-kill curves for *Listeria monocytogenes* and *Pseudomonas aeruginosa*.
Figure 1:
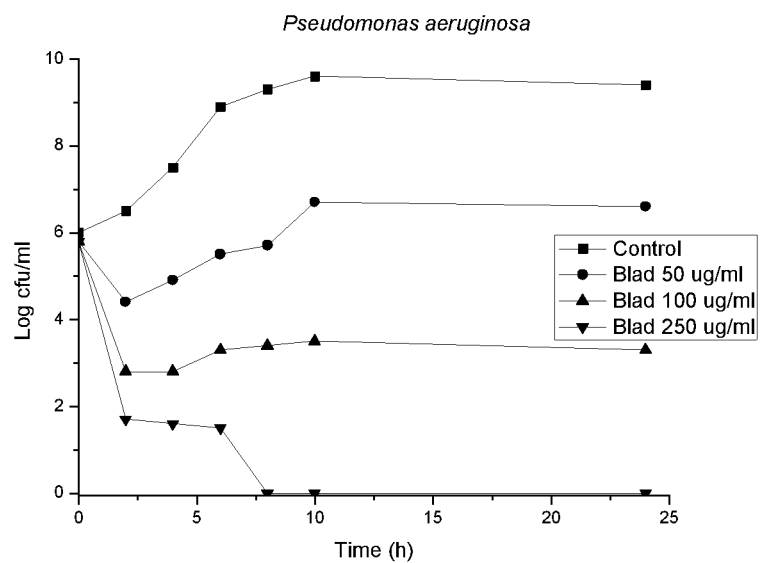

Blad ("banda de *Lupinus albus* doce"—band from sweet *L. albus*) was the name given to a stable and intermediary breakdown product of β-conglutin, the major storage protein present in seeds of the *Lupinus* genus. It was characterised as a 20 kD polypeptide, composed of 173 amino acid residues, and encoded by an internal fragment (519 nucleotides, deposited in GenBank under the accession number ABB 13526) of the gene encoding the precursor of β-conglutin from *Lupinus* (1791 nucleotides, published in GenBank, under the accession number AAS97865). When primers encoding Blad terminal sequences are used to amplify a sequence from genomic *Lupinus* DNA, a ~620 bp product is obtained, indicating the presence of an intron in the gene fragment encoding Blad. Naturally-occurring Blad is the main component of a 210 kD glycooligomer which accumulates exclusively (following intensive limited proteolysis of β-conglutin) in the cotyledons of *Lupinus* species, between days 4 and 12 after the onset of germination. Whilst said oligomer is glycosylated, naturally-occurring Blad is non-glycosylated. The Blad-containing glycooligomer is composed of several polypeptides, the major ones exhibiting molecular masses of 14, 17, 20, 32, 36, 48 and 50 kD. The 20 kD polypetide, Blad, is by far the most abundant polypeptide within the oligomer and appears to be the only one with lectin activity. Naturally-occurring Blad constitutes approximately 80% of the total cotyledonary protein in 8-day old plantlets.

The *L. albus* β-conglutin precursor encoding sequence (SEQ ID NO: 1) is given in FIG. 10. The β-conglutin parent subunit coding sequence is located at residues 70 to 1668. The encoded, 533 amino acid residue β-conglutin parent subunit (SEQ ID NO: 2) is:

```
MGKMRVRFPTLVLVLGIVFLMAVSIGIAYGEKDVLKSHERPEEREQEEWQ
PRRQRPQSRREEREQEQEQGSPSYPRRQSGYERRQYHERSEQREEREQEQ
QQGSPSYSRRQRNPYHFSSQRFQTLYKNRNGKIRVLERFDQRTNRLENLQ
NYRIVEFQSKPNTLILPKHSDADYVLVVLNGRATITIVNPDRRQAYNLEY
GDALRIPAGSTSYILNPDDNQKLRVVKLAIPINNPGYFYDFYPSSTKDQQ
SYFSGFSRNTLEATFNTRYEEIQRIILGNEDEQEYEEQRRGQEQSDQDEG
VIVIVSKKQIQKLTKHAQSSSGKDKPSDSGPFNLRSNEPIYSNKYGNFYE
ITPDRNPQVQDLNISLTYIKINEGALLLPHYNSKAIYVVVVDEGEGNYEL
VGIRDQQRQQDEQEEKEEEVIRYSARLSEGDIFVIPAGYPISINASSNLR
LLGFGINADENQRNFLAGSKDNVIRQLDRAVNELTFPGSAEDIERLIKNQ
QQSYFANGQPQQQQQQQSEKEGRRGRRGSSLPF
```

The internal fragment of the β-conglutin precursor encoding sequence that corresponds to Blad (SEQ ID NO: 3) is given in FIG. 11. The Blad polypeptide (SEQ ID NO: 4) is:

```
RRQRNPYHFSSQRFQTLYKNRNGKIRVLERFDQRTNRLENLQNYRIVEFQ
SKPNTLILPKHSDADYVLVVLNGRATITIVNPDRRQAYNLEYGDALRIPA
GSTSYILNPDDNQKLRVVKLAIPINNPGYFYDFYPSSTKDQQSYFSGFSR
NTLEATFNTRYEEIQRIILGNED
```

The invention relates to a composition comprising an antimicrobial polypeptide comprising Blad or an active variant thereof. It therefore relates to a composition comprising an antimicrobial polypeptide comprising the polypeptide sequence of SEQ ID NO: 4 or an active variant thereof. In alternative embodiments, the composition consists essentially of an antimicrobial polypeptide comprising Blad or an active variant thereof and/or the antimicrobial polypeptide consists essentially of Blad or an active variant thereof. In further embodiments the antimicrobial polypeptide comprising (or consisting essentially of) Blad or an active variant thereof may be used in isolated form.

An active variant of Blad is a variant of Blad that retains the ability to act as an antimicrobial (i.e. has antimicrobial activity—see below for a description of the level of such activity and how to measure it). "An active variant of Blad" includes within its scope a fragment of SEQ ID NO: 4. In preferred embodiments, a fragment of SEQ ID NO: 4 is selected that is at least 10% of the length of SEQ NO: 4, preferably at least 20%, preferably at least 30%, preferably at least 40%, preferably at least 50%, preferably at least 60%, preferably at least 70%, preferably at least 80%, preferably at least 90% and most preferably at least 95% of the length of SEQ NO: 4. Blad or a variant thereof generally has a length of at least 10 amino acid residues, such as at least 20, 25, 30, 40, 50, 60, 80, 100, 120, 140, 160 or 173 amino acid residues.

"An active variant of Blad" also includes within its scope a polypeptide sequence that has homology with SEQ ID NO: 4, such as at least 40% identity, preferably at least 60%, preferably at least 70%, preferably at least 80%, preferably at least 85%, preferably at least 90%, preferably at least 95%, preferably at least 97%, and most preferably at least 99% identity, for example over the full sequence or over a region of at least 20, preferably at least 30, preferably at least 40, preferably at least 50, preferably at least 60, preferably at least 80, preferably at least 100, preferably at least 120, preferably at least 140, and most preferably at least 160 or more contiguous amino acid residues. Methods of measuring protein homology are well known in the art and it will be understood by those of skill in the art that in the present context, homology is calculated on the basis of amino acid identity (sometimes referred to as "hard homology").

The homologous active Blad variant typically differs from the polypeptide sequence of SEQ ID NO: 4 by substitution, insertion or deletion, for example from 1, 2, 3, 4, 5 to 8 or more substitutions, deletions or insertions. The substitutions are preferably 'conservative', that is to say that an amino acid may be substituted with a similar amino acid, whereby similar amino acids share one of the following groups: aromatic residues (F/H/W/Y), non-polar aliphatic residues (G/A/P/I/L/V), polar-uncharged aliphatics (C/S/T/M/N/Q) and polar-charged aliphatics (D/E/K/R). Preferred subgroups comprise: G/A/P; I/L/V; C/S/T/M; N/Q; D/E; and K/R.

An antimicrobial polypeptide comprising Blad or an active variant thereof (as described above) may consist of Blad or an active variant thereof with any number of amino acid residues added to the N-terminus and/or the C-terminus provided that the polypeptide retains antimicrobial activity (again, see below for a description of the level of such activity and how to measure it). Preferably, no more than 300 amino acid residues are added to either or both ends of Blad or an active variant thereof, more preferably no more than 200 amino acid residues, preferably no more than 150 amino acid residues, preferably no more than 100 amino acid residues, preferably no more than 80, 60 or 40 amino acid residues, most preferably no more than 20 amino acid residues.

An antimicrobial polypeptide comprising (or consisting essentially of) Blad or an active variant thereof (as described above) may be utilised in the invention in the form of a purified (e.g. removed from a plant, animal or microbial source) and/or recombinant protein. Production of a recombinant form enables the production of active variants of Blad.

Methods of purifying naturally-occurring Blad are already described in the art (e.g. Ramos et al. (1997) Planta 203(1): 26-34 and Monteiro et al. (2010) PLoS ONE 5(1): e8542). A suitable source of naturally-occurring Blad is a plant of the *Lupinus* genus, such as *Lupinus albus*, preferably a cotyledon of said plant, preferably harvested between about 4 and about 14 days after the onset of germination, more preferably harvested 6 to 12 days after the onset of germination (such as 8 days after the onset of germination). Methods are disclosed in the art for a total protein extraction leading to a crude extract comprising Blad, and for a protein purification of such an extract leading to a partially purified extract, e.g. comprising the Blad-containing glycooligomer that comprises Blad. To isolate Blad itself one can then use SDS-PAGE and/or, preferably, reverse phase (RP)-HPLC on a C-18 column.

An alternative way of obtaining a partially purified extract comprising the glycooligomer that comprises Blad is to utilise the chitin binding activity of Blad. The glycooligomer binds in a very strong manner to a chitin column as part of a chitin affinity chromatography purification, being eluted with 0.05 N HCl. Details of an example of this purification method are as follows:

Cotyledons from eight-day old lupin plants were harvested and homogenized in Milli-Q plus water (pH adjusted to 8.0), containing 10 mM $CaCl_2$ and 10 mM $MgCl_2$. The homogenate was filtered through cheesecloth and centrifuged at 30,000 g for 1 h at 4° C. The pellet was subsequently suspended in 100 mM Tris-HCl buffer, pH 7.5, containing 10% (w/v) NaCl, 10 mM EDTA and 10 mM EGTA, agitated for 1 h at 4° C., and centrifuged at 30,000 g for 1 h at 4° C. The total globulin fraction, contained in the supernatant, was precipitated with ammonium sulphate (561 g/l), left stirring in the cold for 1 h and centrifuged at 30,000 g for 30 min at 4° C. The pellet obtained was dissolved in 50 mM Tris-HCl buffer, pH 7.5, desalted in PD-10 columns equilibrated in the same buffer and passed through a chitin-affinity chromatography column pre-equilibrated in the same buffer. The column was washed with 50 mM Tris-HCl buffer, pH 7.5, and the bound proteins eluted with 0.05 N HCl. The eluted fractions were immediately neutralized with 2 M Tris and the peak fractions pooled, lyophilized and analyzed by SDS-PAGE.

For the preparation of the chitin column, crude chitin was obtained from Sigma and processed as follows: the chitin sample was washed extensively with Milli-Q plus water, followed by 0.05 N HCl. It was then washed with 1% (w/v) sodium carbonate and then with ethanol, until the absorbance of the wash was less than 0.05. Chitin was then packed into a pipette tip and equilibrated with 50 mM Tris-HCl buffer, pH 7.5.

Methods of producing recombinant proteins are well known in the art. Such methods as applied here will involve inserting the polynucleotide encoding a polypeptide comprising Blad or an active variant thereof into a suitable expression vector—enabling the juxtaposition of said polynucleotide with one or more promoters (e.g. an inducible promoter, such as T7lac) and with other polynucleotides or genes of interest—introducing the expression vector into a suitable cell or organism (e.g. *Escherichia coli*), expressing the polypeptide in the transformed cell or organism and removing the expressed recombinant polypeptide from that cell or organism. To assist such purification the expression vector may be constructed such that the polynucleotide additionally encodes, for example, a terminal tag that can assist purification: e.g., a tag of histidine residues for affinity purification. Once the recombinant polypeptide is purified, the purification tag may be removed from the polypeptide, e.g., by proteolytic cleavage.

In a composition comprising an antimicrobial polypeptide comprising (or consisting essentially of) Blad or an active variant thereof, said polypeptide is preferably in partially purified form, more preferably in purified form. Said polypeptide is partially purified when it is present in an environment lacking one or more other polypeptides with which it is naturally associated and/or is represented by at least about 10% of the total protein present. Said polypeptide is purified when it is present in an environment lacking all, or most, other polypeptides with which it is naturally associated. For example, purified Blad means that Blad represents at least about 50%, at least about 60%, at least about 70%, at least about 75%, at least about 80%, at least about 85%, at least about 90%, at least about 95%, at least about 97%, at least about 98%, or at least about 99% of the total protein in a composition.

In a composition comprising an antimicrobial polypeptide comprising (or consisting essentially of) Blad or an active variant thereof, the *Lupinus* protein content may consist essentially of the Blad-containing glycooligomer that comprises a polypeptide that comprises (or consist essentially of) Blad or an active variant thereof.

A composition comprising an antimicrobial polypeptide comprising (or consisting essentially of) Blad may also be a formulation comprising another compound(s) added to the composition by the skilled person. In preferred embodiments, such a formulation is a pharmaceutical formulation comprising an antimicrobial polypeptide comprising (or consisting essentially of) Blad and a pharmaceutically acceptable carrier or diluent.

Microbial Targets

The invention relates to the use of Blad as an antimicrobial compound, i.e. to inhibit the growth of or kill microorganisms that are pathogenic to humans or animals. Such microorganisms include, in particular, bacteria and fungi. Such pathogenic microorganisms are capable of causing infectious disease or any other ill-health (e.g. food poisoning, allergy) in humans and/or animals, and may affect or infect, for example, the eyes, the skin, burns, wounds, the upper respiratory tract, the lungs, the gastrointestinal tract, the genitourinary tract, the kidneys, the liver, the nervous system and/or the cardiovascular system (e.g. the bloodstream). Such pathogenic microorganisms may be inherently pathogenic or may be opportunistic (i.e. do not cause disease in a healthy host but can do in a host with a compromised immune system). Such pathogenic microorganisms may additionally or alternatively cause ill-health by releasing compounds that are toxic to humans or animals.

Blad can be used as an antimicrobial against both Gram-positive and Gram-negative bacterial pathogens. Particularly preferred bacterial targets include pathogenic *Pseudomonas* species, such as *P. aeruginosa*, *Pseudomonas oryzihabitans* and *Pseudomonas plecoglossicida* (most preferably *P. aeruginosa*), pathogenic *Listeria* species, such as *L. monocytogenes* and *Listeria ivanovii* (most preferably *L. monocytogenes*), pathogenic *Bacillus* species such as *B. subtilis*, *Bacillus anthracis* and *Bacillus cereus* (most preferably *B. subtilis*), pathogenic *Staphylococcus* species, such as *S. aureus* (including Methicillin-resistant *Staphylococcus aureus* [MRSA]), *Staphylococcus pseudintermedius*, *Staphylococcus epidermidis*, *Staphylococcus saprophyticus*, *Staphylococcus lugdunensis*, *Staphylococcus schleiferi* and *Staphylococcus caprae* (most preferably *S. aureus*), pathogenic *Salmonella* species, such as *Salmonella enterica* subspecies such as *Salmonella arizonae*, *Salmonella choleraesuis*, *Salmonella enteritidis*, *Salmonella paratyphi* A, *Salmonella paratyphi* B, *Salmonella typhi*, *Salmonella typhimurium*, *Salmonella dublin*, *Salmonella typhisuis* and *Salmonella* brandenburg (most preferably *S. enteritidis* or *S. typhi*) and pathogenic *Campylobacter* species such as *Campylobacter jejuni* and *Campylobacter coli* (most preferably *C. jejuni*). In preferred embodiments Blad is used against pathogens that can cause generalised inflammation and sepsis (e.g. *P. aeruginosa*), Cholera (e.g. *V. cholerae*), Meningitis (e.g. *L. monocytogenes*, *Haemophilus influenzae* type b, *Neisseria meningitidis*, or *Streptococcus pneumoniae*), Pneumonia (e.g. *S. pneumoniae*, *Streptococcus agalactiae* or *S. aureus*), Shigellosis (e.g. *Shigella boydii*, *Shigella dysenteriae*, *Shigella flexneri* or *Shigella sonnei*), Strep throat (e.g. *Streptococcus pyogenes*), Tuberculosis (e.g. *Mycobacterium tuberculosis*, *Mycobacterium bovis*, *Mycobacterium africanum*, *Mycobacterium canetti* and *Mycobacterium microti*), Typhoid (*S. typhi*), or food poisoning (e.g. pathogenic species from one of the following genera: *Listeria*, *Staphylococcus* and *Salmonella*).

Blad can be used as an antimicrobial against both unicellular (yeast) and multicellular (filamentous, mold) fungal pathogens. Particularly preferred fungal targets include pathogenic *Candida* species, such as *C. albicans*, *Candida glabrata*, *Candida lusitaneae*, *Candida parapsilosis*, *Candida tropicalis*, *Candida krusei* and *Candida dubliniensis*, pathogenic *Alternaria* species, such as *A. alternata* and *Alternaria molesta*, pathogenic *Aspergillus* species, such as *A. fumigatus*, *Aspergillus niger*, *Aspergillus flavus* and *Aspergillus clavatus*, pathogenic *Fusarium* species, such as *Fusarium solani*, *Fusarium oxysporum*, *Fusarium verticillioides*, and *Fusarium proliferatum*, pathogenic *Cryptococcus* species, such as *Cryptococcus neoformans*, *Cryptococcus laurentii*, *Cryptococcus albidus* and *Cryptococcus gattii*, and pathogenic *Trichosporon* species, such as *Trichosporon ovoides*, *Trichosporon inkin*, *Trichosporon asahii*, *Trichosporon mucoides*, *Trichosporon asteroides*, and *Trichosporon cutaneum* (all previuosly considered under the general name of *Trichosporon beigelii*), and *Trichosporon dermatis*, *Trichosporon dohaense* and *Trichosporon loubieri*. In preferred embodiments Blad is used against pathogens that can cause invasive fungal infection (IFI), which is usually defined as a systemic, generalized and visceral fungal infection that is often severe and/or life-threatening (in contrast to superficial, local, benign, self-limiting fungal diseases). Particularly preferred IFI causing fungi include pathogenic *Candida*, *Aspergillus* or *Alternaria* species as defined above, preferably *C. albicans*, *A. fumigatus* or *A. alternata*, most preferably *C. albicans* or *A. fumigatus*.

The skilled person will be able to identify, through routine methods, a suitable concentration with which to use an antimicrobial polypeptide comprising (or consisting essentially of) Blad (or an active variant thereof) as an antimicrobial in any particular setting. Preferably, for example, Blad is used at a concentration of at least 1 µg/ml, at least 5 µg/ml, at least 10 µg/ml, at least 20 µg/ml, at least 50 µg/ml, or at least 100 µg/ml, and up to 500 µg/ml, up to 600 µg/ml, up to 1 mg/ml, up to 2.5 mg/ml, up to 5 mg/ml or up to 10 mg/ml. Preferably the concentration of Blad selected is between 10 µg/ml and 5 mg/ml, more preferably between 50 µg/ml and 2.5 mg/ml, more preferably between 100 µg/ml and 1 mg/ml, and even more preferably between 100 µg/ml and 600 µg/ml (such as about 250 µg/ml). The inventors have provided evidence (see Examples 4 and 5) that Blad is non-toxic to the host up to at least 400 µg/ml.

The inventors have surprisingly found that a combination of Blad with a chelating agent (e.g. EDTA) produces a synergistic antimicrobial effect. Therefore, preferably, a chelating agent is used to improve the antimicrobial activity of a polypeptide comprising (or consisting essentially of) Blad (or an active variant thereof), and the use of such a chelating agent may decrease the concentration of said antimicrobial polypeptide required to achieve a particular level of antimicrobial activity. A chelating agent (also known as a chelant, a chelator or a sequestering agent) is any compound that binds to a metal ion to form a non-covalent complex and reduces the ion's activity. Suitable chelating agents include polyamino carboxylates such as EDTA (ethylenediaminetetraacetic acid) and EGTA (ethyleneglycol bis(β-aminoethyl ether)-N,N,N,N-tetraacetic acid). Preferably, EDTA is used as the chelating agent, preferably at a concentration of at least 10 µg/ml, at least 50 µg/ml, or at least 100 µg/ml, and up to 500 µg/ml, up to 1 mg/ml, up to 5 mg/ml, up to 10 mg/ml, or up to 20 mg/ml. Preferably, EDTA is used at a concentration of between 0.1 mg/ml and 1 mg/ml.

Outcomes

The antimicrobial polypeptide comprising (or consisting essentially of) Blad (or an active variant thereof) may be used to inhibit the growth of a human/animal pathogenic microorganism (meaning that it has microbistatic activity) and/or to kill said microorganism (meaning that it has microbicidal activity). The skilled person will be able to identify a suitable dose and/or concentration to obtain a particularly desired growth inhibition or killing of the microorganism.

Preferably, when used as a microbistatic agent, the antimicrobial polypeptide reduces the rate of growth by 10%, more preferably by 50%, more preferably by 75%, more preferably by 90%, more preferably by 95%, more preferably by 98%, more preferably by 99%, and even more preferably by 99.9% in comparison to equivalent conditions where the antimicrobial polypeptide is not present. Most preferably the antimicrobial polypeptide prevents any growth of the microorganism.

Preferably, when used as a microbicidal agent, the antimicrobial polypeptide kills 10% of the population of the microorganisms, more preferably 50% of said population, more preferably 75% of said population, more preferably 90% of said population, more preferably 95% of said population, more preferably 98% of said population, more preferably 99% of said population, and even more preferably by 99.9% of said population in comparison to equivalent conditions where the antimicrobial polypeptide is not present. Most preferably the antimicrobial polypeptide kills all of the population of the microorganism.

When used to prevent or treat an infection in or on a human or animal the antimicrobial polypeptide is preferably used in a therapeutically effective amount, that is to say an amount that provides a level of growth inhibition and/or killing of a microorganism such that a clinically detectable level of infection prevention or abrogation is achieved. Preferably, the therapeutically effective amount of the antimicrobial polypeptide is non-toxic to the human or animal subject. It is intended that said therapeutically effective amount of the antimicrobial polypeptide is therapeutically effective when administered as part of a composition comprising the antimicrobial polypeptide.

The inventors have surprisingly found that, at similar concentrations (by mass), Blad is approximately as potent as amphotericin B and more potent than fluconazole against *C. albicans* and *A. fumigatus* (in terms of fungicidal and fungistatic activity). This is a striking result given (i) the much greater molecular mass of Blad in comparison to the relatively small organic molecules of amphotericin B and fluconazole and (ii) the non-toxic and edible nature of Blad to humans and other animals.

Medical Uses and Methods

The inventors provide a composition comprising an antimicrobial polypeptide comprising Blad or an active variant thereof for use in a method of treatment of the human or animal body by therapy or prophylaxis. To this end they also provide a method of treating a human or animal comprising administering to a subject in need thereof a composition comprising a therapeutically effective amount of an antimicrobial polypeptide comprising Blad or an active variant thereof.

The inventors also provide a composition comprising an antimicrobial polypeptide comprising Blad or an active variant thereof for use in a method of preventing or treating an infection in or on a human or animal subject by a microorganism. To this end they also provide:

a method of preventing or treating an infection by a microorganism comprising administering to a subject in need thereof a composition comprising a therapeutically effective amount of an antimicrobial polypeptide comprising Blad or an active variant thereof and use of a composition comprising an antimicrobial polypeptide comprising Blad or an active variant thereof in the manufacture of a medicament for preventing or treating an infection in or on a human or animal subject by a microorganism.

Said composition may be administered by injection (such as intradermal, subcutaneous, intramuscular, intravenous, intraosseous, and intraperitoneal), transdermal particle delivery, inhalation, topically, orally or transmucosally (such as nasal, sublingual, vaginal or rectal).

Preferably, said composition comprises a pharmaceutically acceptable carrier or diluent. Such a pharmaceutical composition may be formulated as a conventional pharmaceutical preparation. This can be done using standard pharmaceutical formulation chemistries and methodologies, which are available to those skilled in the art. For example, an antimicrobial polypeptide comprising Blad (or an active variant thereof) can be combined with one or more pharmaceutically acceptable carriers or diluents to provide a liquid preparation. Auxiliary substances, such as wetting or emulsifying agents, pH buffering substances and the like, may also be present.

The carriers, diluents and auxiliary substances are generally pharmaceutical agents which may be administered without undue toxicity and which will not in themselves induce an immune response in the individual receiving the composition. Pharmaceutically acceptable carriers include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. It is also preferred, although not required, that the preparation will contain a pharmaceutically acceptable carrier that serves as a stabilizer, particularly advantageous for a composition comprising a polypeptide like Blad. Examples of suitable carriers that also act as stabilizers for polypeptides include, without limitation, pharmaceutical grades of dextrose, sucrose, lactose, trehalose, mannitol, sorbitol, inositol, dextran, and the like. Other suitable carriers include, again without limitation, starch, cellulose, sodium or calcium phosphates, citric acid, tartaric acid, glycine, high molecular weight polyethylene glycols (PEGs), and combination thereof.

Once formulated, the composition can be delivered to a subject in vivo using a variety of known routes and techniques. For example, the liquid preparations can be provided as an injectable solution, suspension or emulsion and administered via parenteral, subcutaneous, intradermal, intramuscular, intravenous, intraosseous or intraperitoneal injection using a conventional needle and syringe, or using a liquid jet injection system. Liquid preparations can also be administered topically to the eyes, to skin, hair or mucosal tissue (e.g. nasal, sublingual, vaginal or rectal), or provided as a finely divided spray suitable for respiratory or pulmonary administration. Other modes of administration include oral administration, suppositories, and active or passive transdermal delivery techniques. In preferred embodiments the antimicrobial polypeptide is formulated into a composition suitable as a topical lotion, hand-cream, eye-drop solution, shampoo or conditioner.

The subject in need of the antimicrobial polypeptide may be any human or animal individual. In preferred embodiments the antimicrobial polypeptide may be used to prevent infection in subjects at particular risk of acquiring an infection by a microorganism and/or to treat infection in subjects at particular risk of being unable to clear a microbial infection without medical intervention, such as the young (such as an individual below the age of 16 years, such as an individual below the age of 5 years, 3 years, 2 years, 1 year, 6 months or 1 month), the elderly (such as an individual above the age of 70 years, such as an individual above the age of 80 years or 90 years), those with a compromised immune system (such as those with a primary immunodeficiency, those with an acquired immunodeficiency (e.g. those with AIDS) and those with a suppressed immune system as a result of treatment such as chemotherapy or immunosuppressive drug regimes), those who are critically ill, or those who might have a particularly high exposure to pathogenic microorganisms (e.g. medical professionals).

Other Antimicrobial Uses and Methods

The inventors also provide the use of a composition comprising an antimicrobial polypeptide comprising Blad or an active variant thereof to kill, or inhibit the growth of, a microorganism that is pathogenic to a human or an animal at a site that is not on or in the human or animal body. To this end they also provide a method of killing or inhibiting the growth of a microorganism that is pathogenic to a human or an animal at a site that is not on or in the human or animal body, said method comprising administering to said site a composition comprising an effective amount of an antimicrobial polypeptide comprising Blad or an active variant thereof. Said effective amount is an amount that provides a level of growth inhibition and/or killing of a microorganism such that a detectable level of prevention or abrogation of microbial colonisation is achieved. Preferably, the effective amount of the antimicrobial polypeptide is non-toxic to the human or animal subject. It is intended that said effective amount of the antimicrobial polypeptide is effective when administered as part of a composition comprising the antimicrobial polypeptide.

In these embodiments it is intended that the antimicrobial polypeptide is used as a disinfectant to prevent the growth of and/or kill a pathogenic microorganism on an article that is to be ingested by, or placed directly on or in, a human or animal, or a surface that is in need thereof (e.g. a surface that may, directly or indirectly, come into contact with a human or animal) so that the risk is of:

(i) a human or animal becoming infected with said pathogenic microorganism; or (ii) a human or animal coming into contact with a toxin released by a pathogenic microorganism; is reduced.

In preferred embodiments the antimicrobial polypeptide is used within or on a foodstuff to prevent the growth of a human/animal pathogenic microorganism on or within that foodstuff or to kill a human/animal pathogenic microorganism already present on or within that foodstuff. In this way the antimicrobial polypeptide can be used to reduce the risk of a human or animal becoming infected with a pathogenic microorganism, or of a human or animal ingesting a toxin released by a pathogenic microorganism, as a result of ingesting that foodstuff. In these embodiments it is particularly preferred that said pathogenic microorganism is capable of causing food poisoning (e.g. directly or via a released toxin). By foodstuff it is intended to mean any liquid or solid substance intended for consumption for nutritional or pleasurable reasons. The composition comprising the antimicrobial polypeptide can for example be mixed with other components of the foodstuff during the preparation for the foodstuff or may for example be applied to the surface of the foodstuff (for example as a liquid film or a spray). Particular foodstuffs considered in these embodiments include water, soft drinks such as fruit juices, alcoholic drinks, raw meat, cooked poultry meat, eggs, milk, cream, ice-cream, cheese, raw vegetables and fruits, processed foods (particularly relevant to e.g. *L. monocytogenes, V. cholerae*, pathogenic *Staphylococcus* species, pathogenic *Salmonella* species and pathogenic *Campylobacter* species), and nuts and starchy foods such as bread, rice and potatoes (particularly relevant for pathogenic *Aspergillus* species).

In alternative preferred embodiments the antimicrobial polypeptide is used within or on a medical device or instrument—any device placed on or within the body to carry out a diagnostic, therapeutic or surgical function— such as artificial body tissue, pacemakers, stents, scaffolds, valves, thermometers, syringes, hypodermic needles, monitoring equipment, ventilators, cardiac defibrillators, heart lung machines, EEG and ECG units, ultrasound devices, drills, saws, knives, scalpels, tongues, scissors, clips and stitches and the like. In such a way the antimicrobial polypeptide can be used to prevent infection of a body that comes into contact with a device or instrument during a medical procedure.

In alternative preferred embodiments the antimicrobial polypeptide is used on a surface that is in need thereof (e.g. a surface that may, directly or indirectly, come into contact with a human or animal). The surface to which the antimicrobial polypeptide may be applied may be located within an environment where:

(a) medical examination, diagnosis or treatment is to take place;

(b) a foodstuff is to be prepared or otherwise handled or stored;

(c) personal washing and/or sanitation is to take place; and/or (d) a person at particular risk of
   (i) acquiring an infection by a microorganism; and/or
   (ii) being unable to clear a microbial infection without medical intervention; is situated (and examples of such persons are described above).

Examples of such surfaces include any within an industrial food factory and shelves/benches within a food supermarket.

The surface to which the antimicrobial polypeptide may be applied may be a floor or wall of a building (or a room thereof) or a surface of an article within said room or building. Particular buildings envisaged include hospitals and other healthcare buildings, schools and other child-care centres, elderly care buildings, restaurants and other eateries, places of food preparation, processing and/or storage (e.g. markets, foodstores, supermarkets, and industrial food factories), and private dwellings. Particular rooms envisaged include all of those within a healthcare setting, especially operating theatres, accident and emergency departments, intensive care and patient wards, as well as kitchens, bathrooms, toilets, restaurants and food preparation/processing halls.

EXAMPLES

In the following Examples BLAD denotes the naturally-occurring Blad-containing glycooligomer comprising the 20 kD Blad polypeptide, purified as per Ramos et al. (1997) Planta 203(1): 26-34: see "Plant material and growth conditions" and "Purification of proteins" parts of the Materials and Methods section of that document.

Definitions:

MIC—Minimum Inhibitory Concentration: the lowest concentration of an antimicrobial that inhibits the visible growth of a microorganism.

MFC/MBC—Minimum Fungicidal/Bactericidal Concentration (or Minimal Lethal Concentration): the lowest concentration of an antimicrobial agent needed to kill 99.9% of the initial inoculum after 24 h under a standardized set of conditions.

Time-kill curves—Determination of the "killing" of an isolate over time by one or more antimicrobial agents under controlled conditions is known as the time-kill method. It is a broth based method where the rate of killing of a fixed inoculum is determined by sampling control (organism, no drug) and antimicrobial agent-containing tubes or flasks, at certain time intervals, and determining the survivor colony count (cfu/ml) by spreading each sample onto an agar plate.

Example 1—Bactericidal Activity of BLAD

MIC and MBC of BLAD for Various Bacterial Species (Using Mueller-Hinton Medium):

| Bacterial Species | MIC (µg/ml) | MBC (µg/ml) |
|---|---|---|
| Pseudomonas aeruginosa | 32-256 | 128-256 |
| Listeria monocytogenes | 8 | >512 |
| Bacillus subtilis | 4 | >512 |
| Staphylococcus aureus | 8 | >512 |
| Salmonella thyphimurium | 64 | 128 |

Time-Kill curves for BLAD with (A) *Listeria monocytogenes* and (B) *Pseudomonas aeruginosa*: see FIG. 1.

Against *L. monocytogenes* and *P. aeruginosa* BLAD is bacteriostatic at 100 µg/ml and bactericidal at 250 µg/ml.

Figure 2:
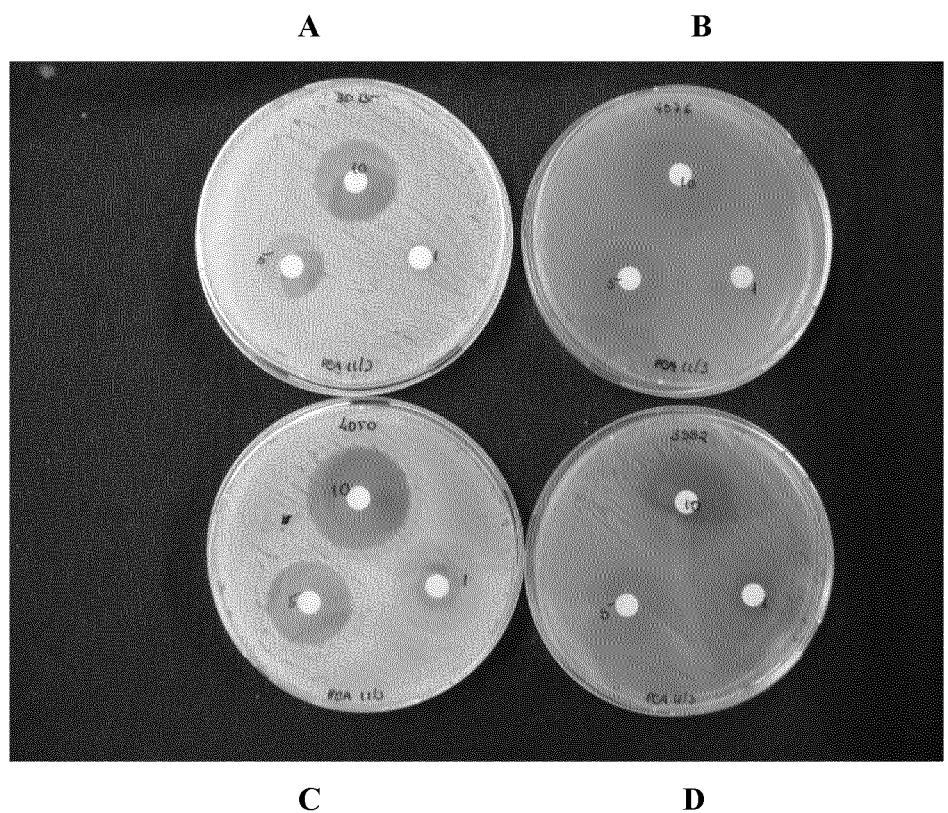
FIG. 2 shows inhibition halos for *Staphylococcus aureus, Bacillus subtilis, P. aeruginosa* and *L. monocytogenes*.

Inhibition halo data for BLAD against (A) *Staphylococcus aureus*, (B) *Bacillus subtilis*, (C) *Pseudomonas aeruginosa*, and (D) *Listeria monocytogenes*: see FIG. 2.

Growth of all tested bacterial species on PCA was increasingly inhibited with increasing BLAD amounts on the treatment disks, from 20 µg (lower right disks) to 100 µg (lower left disks) and to 200 µg (top disks) (incubation 24 h—the effects were seen for several days).

Example 2—Fungicidal Activity of BLAD

MIC and MFC of BLAD for *Candida* Species (Using RPMI Medium)

| Candida Species | MIC (µg/ml) | MFC (µg/ml) |
|---|---|---|
| Candida albicans | 16-32 | 256 |
| Candida dubliniensis | 32-64 | 256 |
| Candida glabrata | 1-2 | >512 |
| Candida lusitaneae | 32-64 | >512 |
| Candida parapsilosis | 32 | >512 |
| Candida tropicalis | 16-32 | >512 |

MIC and MFC of BLAD for *Candida* Species (Using PDB Medium at pH 7.5)

| Candida Species | MIC (µg/ml) | MFC (µg/ml) |
|---|---|---|
| Candida albicans | 2-4 | 4-8 |
| Candida dubliniensis | 2-4 | 8 |
| Candida glabrata | 2 | 16-64 |
| Candida lusitaneae | 2-4 | 8-32 |
| Candida parapsilosis | 2-4 | 64 |
| Candida tropicalis | 4 | 4-16 |

MIC and MFC of BLAD for Various Filamentous Fungi (Using RPMI Medium)

| Fungal Species | MIC (µg/ml) | MFC (µg/ml) |
|---|---|---|
| Alternaria sp. | 64 | >512 |
| Aspergillus fumigatus | 32 | >512 |
| Aspergillus niger | 32-64 | >512 |
| Botrytis cinerea | 128 | 512 |
| Colletotrichum acutatum | 64 | >512 |
| Colletotrichum gloesporioides | 64 | >512 |
| Fusarium oxysporum | 64 | >512 |

NB—MIC for *Cryptococcus neoformans* measured at 0.25-1.0 µg/ml.

Figure 3:
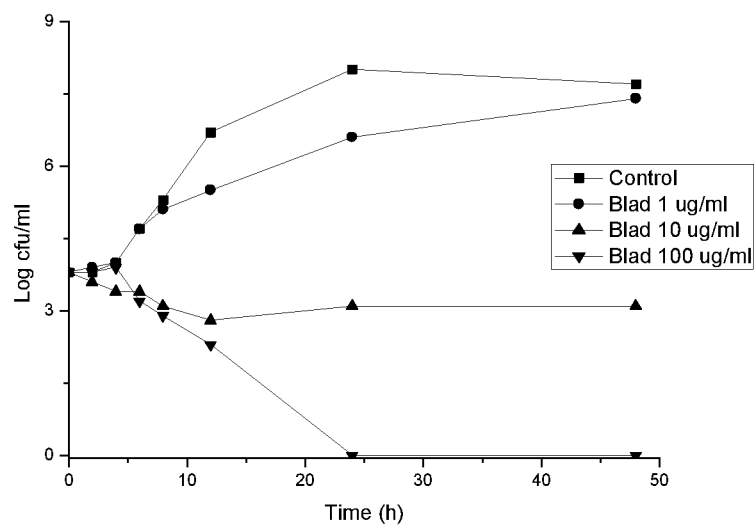
FIG. 3A shows a time-kill curve for *C. albicans*.
FIGS. 3B and 4 show growth curves for *C. albicans*.
Figure 3:
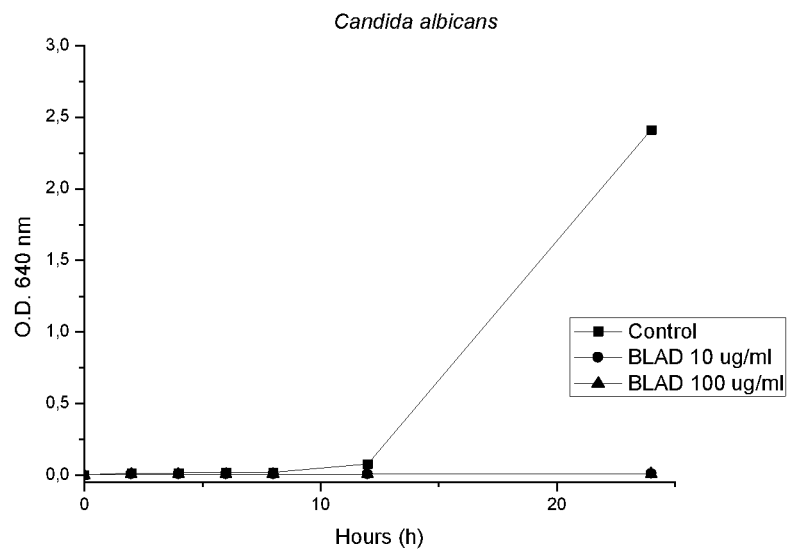

Time-kill curve (A) and growth curve (B) for BLAD with *Candida albicans* in PDB medium: see FIG. 3.

Against *C. albicans* BLAD is fungistatic at 10 µg/ml and fungicidal at 100 µg/ml.

Figure 4:
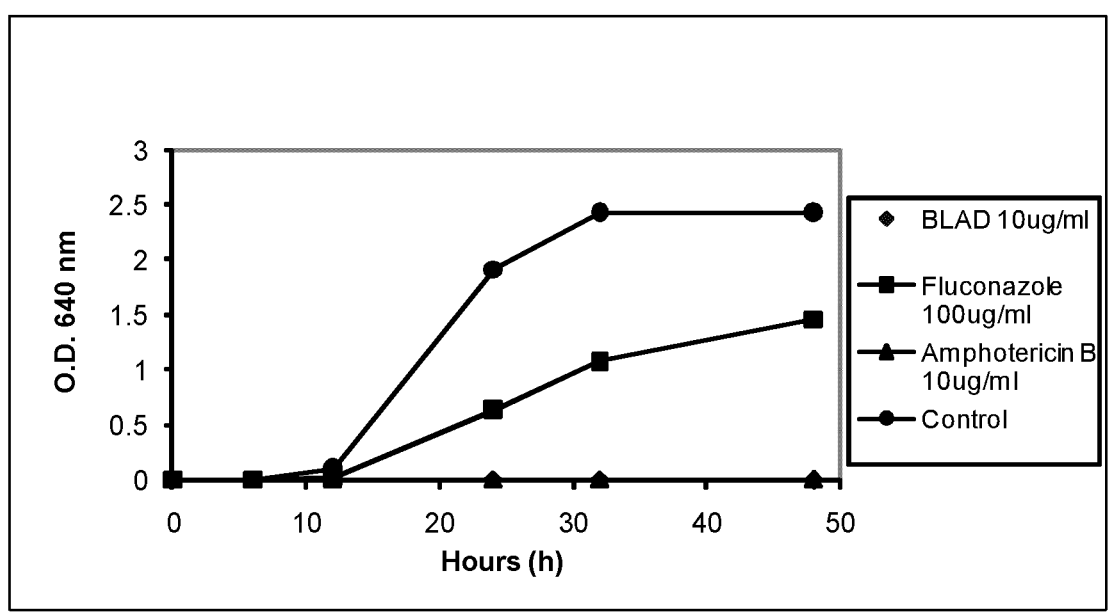

Growth curve for BLAD with *Candida albicans* in PDB pH 7 Medium: see FIG. 4.

Against *C. albicans* BLAD and amphotericin B are fungistatic at 10 µg/ml. At 100 µg/ml fluconazole merely delays growth.

Figure 5:
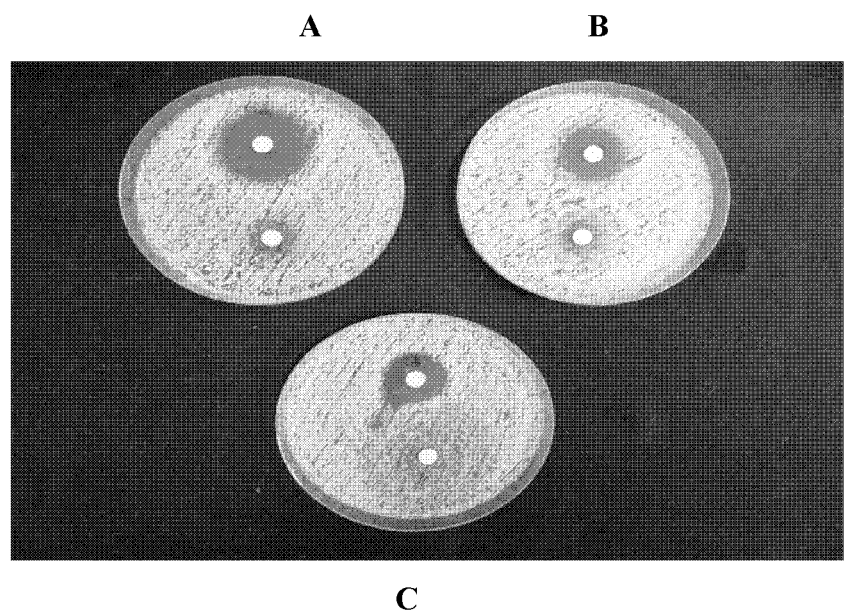
FIGS. 5 to 8 collectively show inhibition halos for *C. albicans, Cryptococcus neoformans* and *A. fumigatus*.

Inhibition halo data for (A and B) BLAD and (C) amphotericin B or fluconazole against *Candida albicans*: see FIG. 5.

Growth of *C. albicans* on Potato Dextrose Agar (PDA) pH 7.5 was inhibited with increasing BLAD amounts on the treatment disks, from 20 µg (A, lower disk) to 50 (B, lower disk) to 100 µg (B, upper disk) and to 200 µg (A, upper disk) (incubation 3 days). This compares very favourably with the inhibition achieved with 20 amphotericin B (C, upper disk) and 25 µg fluconazole (C, lower disk).

Figure 6:
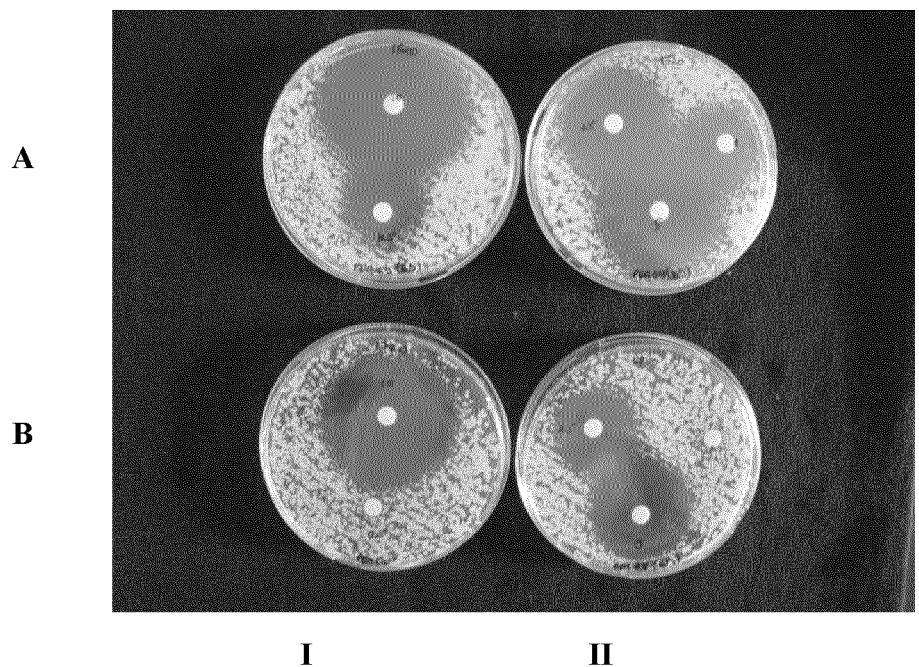

Inhibition halo data for BLAD against *Cryptococcus neoformans* on (A) PDA and (B) PDA pH 7.5 (3 Day Incubation): see FIG. 6.

Growth of *C. neoformans* was inhibited on both media with increasing BLAD amounts on the treatment disks, though with greater efficacy on PDA. I—top disks 200 µg, bottom disks 10 µg; II—upper left disks 50 µg, upper right disk 20 µg, lower disk 100 µg.

Figure 7:
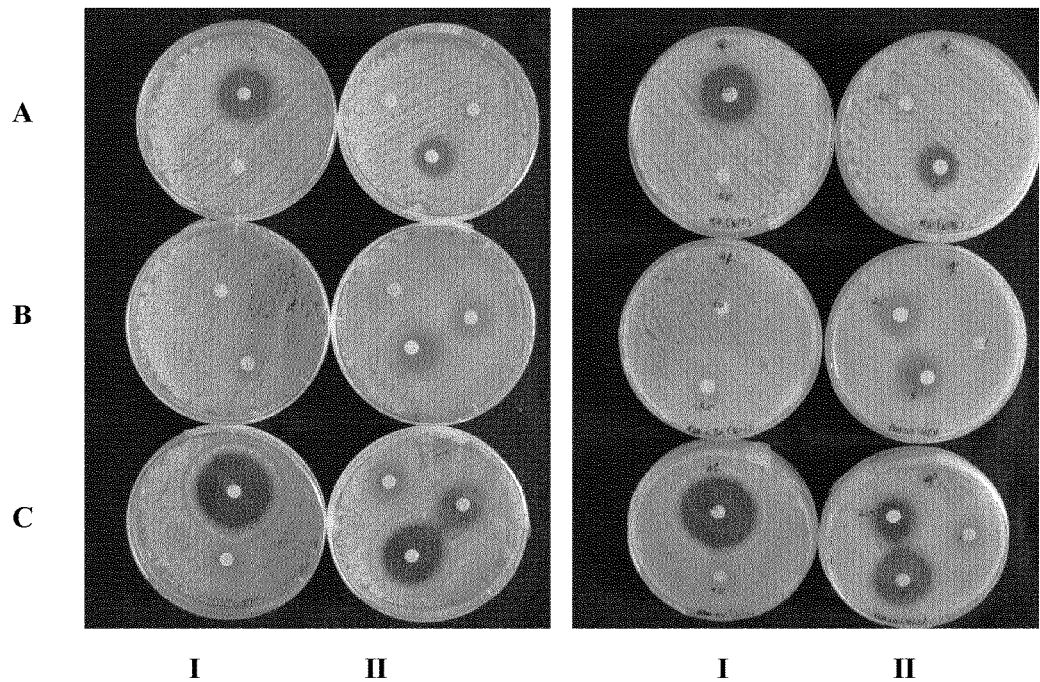

Inhibition halo data for BLAD against *Aspergillus fumigatus* on (A) Mueller-Hinton medium (rule M44-A), (B) PDA or (C) PDA pH 7.5 (3 day incubation): see FIG. 7. Left panel shows plates seen from above; right panel shows plates seen from below.

Growth of *A. fumigatus* was inhibited on all media with increasing BLAD amounts on the treatment disks, though with greatest efficacy on PDA pH 7.5. I—top disks 200 µg, bottom disks 10 µg; II—upper left disks 50 µg, upper right disk 20 µg, lower disk 100 µg.

Figure 8:
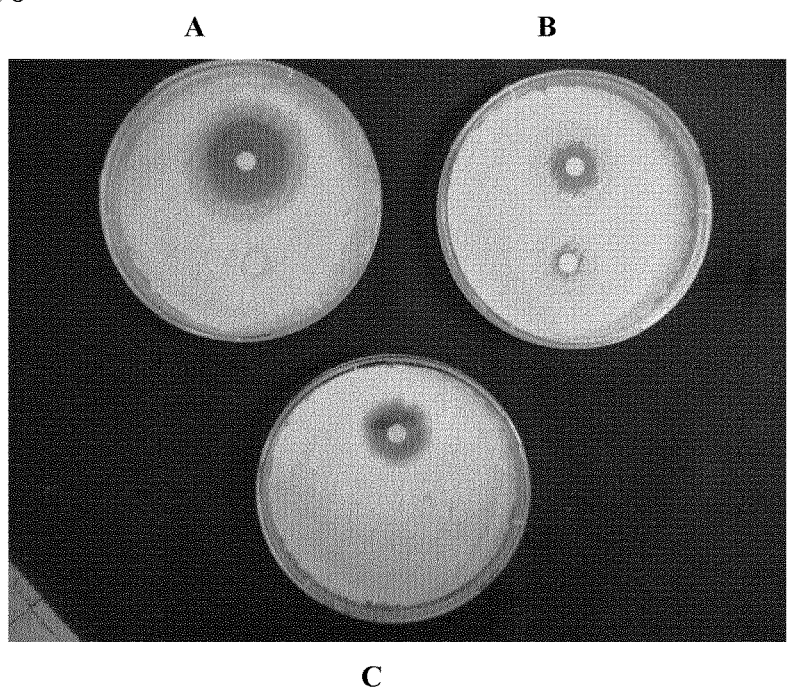

Inhibition Halo Data for (A and B) BLAD and (C) Amphotericin B or Fluconazole Against *Aspergillus fumigatus* on PDA pH 7.5 (6 Day Incubation): See FIG. 8.

Growth of *A. fumigatus* on PDA pH 7.5 was inhibited with increasing BLAD amounts on the treatment disks, from 20 µg (A, lower disk) to 50 µg (B, lower disk) to 100 µg (B, upper disk) and to 200 µg (A, upper disk). This compares very favourably with the inhibition achieved with 10 mg amphotericin B (C, upper disk) and 100 mg fluconazole (C, lower disk). Very similar results were seen for *Trichosporon cutaneum* (data not shown).

Figure 9:
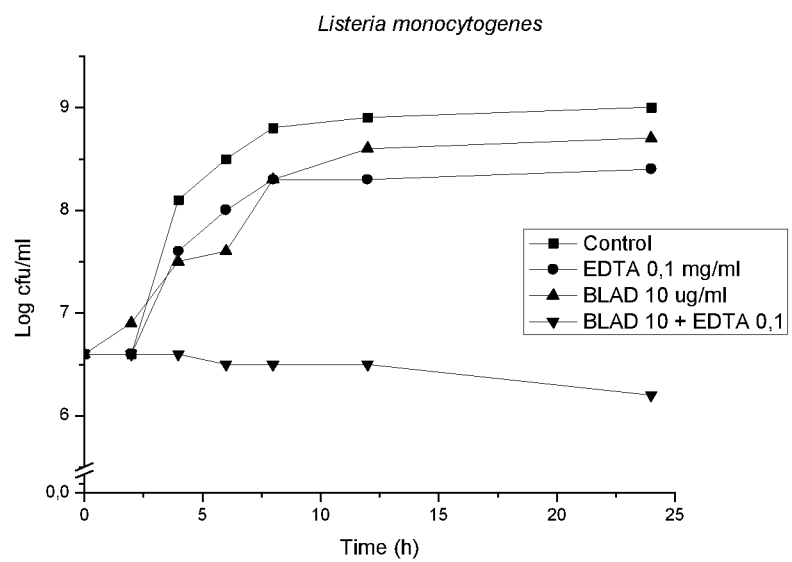
FIG. 9 shows time-kill curves for *L. monocytogenes, P. aeruginosa* and *C. albicans*.
Figure 9:
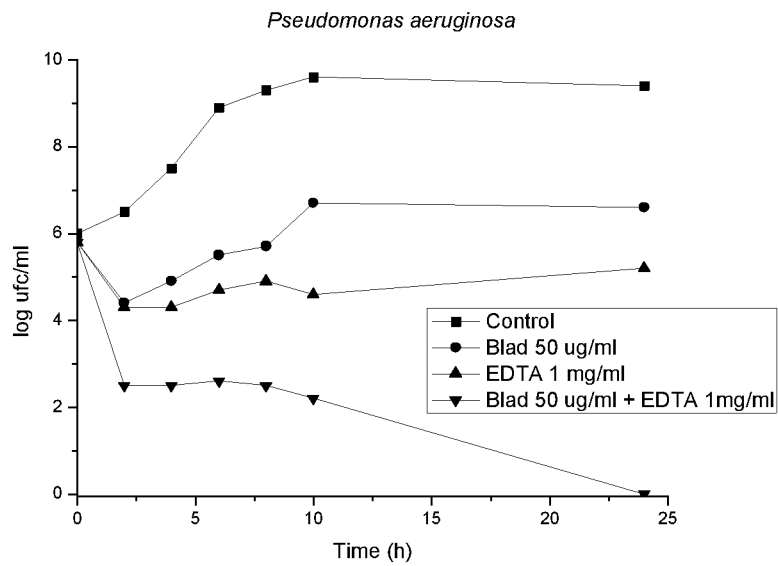
Figure 9:
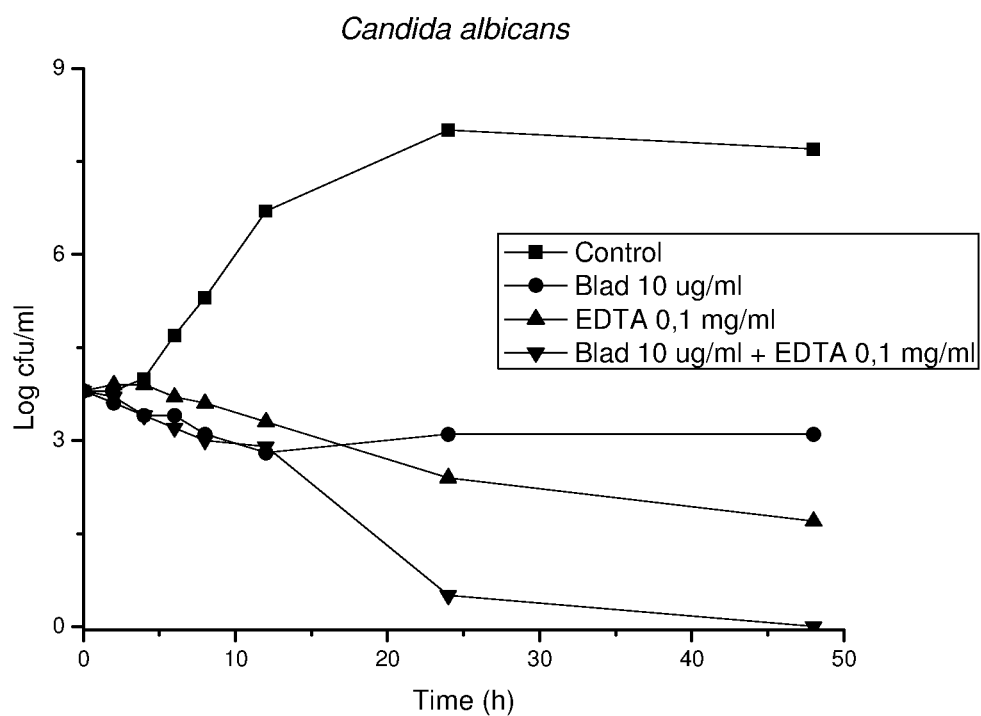

Example 3—Synergistic Effect of EDTA with BLAD with Respect to Bactericidal/Fungicidal Activity Against Human Pathogens Time-kill curves for BLAD and/or EDTA with (A) *Listeria monocytogenes*, (B) *Pseudomonas aeruginosa* and (C) *Candida albicans*: see FIG. 9.

Against *L. monocytogenes* neither BLAD at 10 µg/ml nor EDTA at 0.1 mg/ml inhibits growth but a combination of the two is bacteriostatic. Against *P. aeruginosa* BLAD at 50 µg/ml or EDTA at 1 mg/ml inhibits growth (i.e. both are bacteriostatic) but a combination of the two is bactericidal. Against *C. albicans* BLAD at 10 µg/ml or EDTA at 0.1 mg/ml inhibits growth (i.e. both are fungistatic) but a combination of the two is fungicidal.

Example 4—Dermal Toxicity Study of BLAD in Guinea Pigs

Confidential study carried out at the Faculty of Veterinary Medicine, Technical University of Lisbon, on behalf of Instituto Superior de Agronomia (Jul. 18, 2006-Aug. 1, 2006) using OECD Guideline for testing of chemicals, No. 402, Acute Dermal Toxicity. The study was conducted in accordance with good laboratory practice and animal welfare.

The acute dermal toxicity of BLAD was evaluated after single dose exposure in guinea pigs, which are widely accepted as suitable animals for dermal toxicity studies. BLAD was applied to the glabrous skin in two groups of 10 animals each, with dosing at 200 µg/ml and 400 µg/ml respectively. After exposure the animals were kept under observation for a period of 15 days, during which body mass, morbidity and mortality were recorded.

Materials and Methods—
1. Materials
Test item: BLAD was supplied at 5 mg/ml (yellowish opaque liquid, 0-4° C.) and stored at −80° C.
Animals: albino guinea pigs; strain: Dunkin Hartley (Hsd-Poc: DH) by Harlan *Iberica*, Barcelona.
Number of animals used: 30; body weight: 400-449 g; age: 6 weeks.
Lodging: the animals were individually placed in polyethylene boxes with sterilized wood shavings (Lignocel).
Ambient Conditions:
a) Photoperiod: cycles of light/dark for 12 h in 12 h.
b) Controlled environment: an average temperature of 19/22° C. and average humidity of 60%.
Adaptation: the animals were kept under environmental conditions of the test for seven days before the start of the test.
Food: Global Diet 2014, Rodent Maintenance Diet supplied by Harlan Iberica, Barcelona; water ad libitum.
2. Methods
Administration: animals were shaved 48 h before the test and only animals that had lesion-free skin were taken forward in the study. An aliquot of 1 ml (at either 200 µg/ml or 400 µg/ml) was applied to the shaved skin of each animal.
Study design: the 30 animals of the study were divided into four groups, two groups of ten animals each and two groups with five animals each. A group of ten animals was exposed to BLAD at 200 µg/ml (test group 1) and another group of ten animals was exposed to BLAD at 400 µg/ml (test group 2). The two groups of five animals served as controls: one group was exposed to water (1 ml aliquot) whilst another group was not subjected to any administration but handled as per all the other groups.

Outcomes: after exposure the animals were observed daily for 15 days to record any signs of morbidity or even death. In terms of morbidity particular attention was paid to possible appearance of skin lesions at the site of exposure and possible signs of general toxicity such as changes in normal behavior patterns. Body weight was individually assessed before exposure and at the end of test period.

Results—
At neither concentration of BLAD were there signs of any physical changes in the dermal administration area or changes in drinking/feeding or general behavior. No adverse reactions or death occurred upon BLAD administration. Increase in body mass was similar in all groups (and was consistent with the increase expected from developing animals of such young age).

Conclusions—BLAD at concentrations up to 400 µg/ml (and possibly higher) does not show dermal toxicity.

Example 5—Oral Toxicity Study of BLAD in Albino Rats

Confidential study carried out at the Faculty of Veterinary Medicine, Technical University of Lisbon, on behalf of Instituto Superior de Agronomia, using OECD Guideline for testing of chemicals, No. 401, Acute Oral Toxicity. The study was conducted in accordance with good laboratory practice and animal welfare.

The acute oral toxicity of BLAD was evaluated after single dose exposure in rats, which are widely accepted as suitable animals for oral toxicity studies. BLAD was administered by gavage in two groups of 10 animals each, with dosing at 200 µg/ml and 400 µg/ml respectively. After exposure the animals were kept under observation for a period of 15 days, during which body mass, morbidity and mortality were recorded. After the observation period the animals were euthanized and underwent necropsy.

Materials and Methods—
1. Materials
Test item: BLAD was supplied at 5 mg/ml (yellowish opaque liquid, 0-4° C.) and stored at −80° C.
Animals: *Rattus norvegicus*, strain: Wistar Hannover, acquired by the vivarium of the Faculty of Veterinary Medicine of Lisbon from Harlan *Iberica*, Barcelona.
Number of animals used: 30; body weight: 250-300 g; age: 10 weeks.
Lodging: the animals were individually placed in polyethylene boxes with sterilized wood shavings (Lignocel).
Ambient Conditions:
a) Photoperiod: cycles of light/dark for 12 h in 12 h.
b) Controlled environment: an average temperature of 19/22° C. and average humidity of 60%.
Adaptation: the animals were kept under environmental conditions of the test for seven days before the start of the test.
Food: Global Diet 2014, Rodent Maintenance Diet supplied by Harlan *Iberica*, Barcelona; water ad libitum.
2. Methods
Administration: an aliquot of 1 ml (at either 200 µg/ml or 400 µg/ml) was applied to each animal by oral (oro-esophageal) intubation, commonly known as gavage. The administration was carried out with a metal probe appropriate to the species of animal used. The animals were subjected to fasting for 18 h prior to administration and fed 3 h following administration.

Study design: the 30 animals of the study were divided into four groups, two groups of ten animals each and two groups with five animals each. A group of ten animals was exposed to BLAD at 200 μg/ml (test group 1) and another group of ten animals was exposed to BLAD at 400 μg/ml (test group 2). The two groups of five animals served as controls: one group was exposed to water (1 ml aliquot) whilst another group was not subjected to any administration but handled as per all the other groups.

Outcomes: after administration the animals were observed daily for 15 days to record any signs of morbidity or even death. Body weight was individually assessed before exposure and at the end of test period. After the observation period the animals were euthanized (by asphyxiation in an atmosphere saturated with carbon dioxide) for subsequent post-mortem examination.

Results—

At neither concentration of BLAD were there signs of any physical changes or changes in drinking/feeding or general behavior. No adverse reactions or death occurred upon BLAD administration. Increase in body mass was similar in all groups (and was consistent with the increase expected from developing animals of such young age). Necropsy/macroscopic observation of the organs of the thoracic and abdominal cavity revealed no changes thereto.

Conclusions—BLAD at concentrations up to 400 μg/ml (and possibly higher) does not show oral toxicity.

The invention claimed is:

1. A method of treating a bacterial infection, comprising identifying that a bacterial infection in or on a human or animal subject is caused by a bacterium selected from the group consisting of *Pseudomonas aeruginosa*, *Listeria monocytogenes*, *Bacillus subtilis* or *Staphylococcus aureus* and *Salmonella thyphimurium*; and administering to the subject in need thereof, by a route or technique capable of reaching the site of infection, a composition comprising the Blad polypeptide comprising the amino acid sequence of SEQ ID NO:4 at a concentration range having a lower range limit not less than the following to inhibit the causative bacterium: 32 µg/mL for *Pseudomonas aeruginosa*, 8 µg/mL for *Listeria monocytogenes*, 4 µg/mL for *Bacillus subtilis*, 8 µg/mL for *Staphylococcus aureus* and 64 µg/mL for *Salmonella thyphimurium*.

2. The method according to claim 1 wherein the composition further comprises a pharmaceutically acceptable carrier or diluent.

3. The method according to claim 1 wherein the composition further comprises a chelating agent.

4. The method according to claim 1 wherein the subject has a compromised immune system or is critically ill.

5. A method of inhibiting the growth of, or killing a bacterium, comprising identifying that a bacterium pathogenic to a human or an animal at a site that is not on or in the human or animal body is caused by a bacterium selected from the group consisting of *Pseudomonas aeruginosa*, *Listeria monocytogenes*, *Bacillus subtilis* or *Staphylococcus aureus* and *Salmonella thyphimurium*; and administering to the site a composition comprising the Blad polypeptide comprising the amino acid sequence of SEQ ID NO:4 at a concentration range having a lower range limit not less than the following to inhibit the causative bacterium: 32 µg/mL for *Pseudomonas aeruginosa*, 8 µg/mL for *Listeria monocytogenes*, 4 µg/mL for *Bacillus subtilis*, 8 µg/mL for *Staphylococcus aureus* and 64 µg/mL for *Salmonella thyphimurium*.

6. The method according to claim 5 wherein said composition is used to disinfect, with respect to a human or animal pathogenic bacterium, an article that is to be ingested by, or placed directly on or in, a human or animal, or a surface that is in need thereof.

7. The method according to claim 6 wherein said article is a foodstuff or a medical device or instrument.

8. The method according to claim 6 wherein said surface is located within an environment where:
    (a) medical examination, diagnosis or treatment is to take place;
    (b) a foodstuff is to be prepared or otherwise handled or stored;
    (c) personal washing and/or sanitation is to take place; and/or
    (d) a person at particular risk of
        (i) acquiring an infection by a bacterium; and/or
        (ii) being unable to clear a microbial infection without medical Intervention.

9. The method according to claim 5 wherein said composition further comprises a chelating agent.

* * * * *

SEQUENCE LISTING

<160> NUMBER OF SEQ ID NOS: 4

<210> SEQ ID NO 1
<211> LENGTH: 1791
<212> TYPE: DNA
<213> ORGANISM: Lupinus albus

<400> SEQUENCE: 1

```
gatggcgatg aatgaacact gcgtttgctg gctttgatga aaatcgagtg caacctaata      60
taatcaaata tgggtaagat gagagtgagg tttccaacgt tagtgttggt actaggaata     120
gtattcctca tggcagtgtc aattggtatt gcttatggag aaaaagatgt gctaaagagt     180
catgagaggc ctgaggaaag agaacaagag gagtggcaac ctaggagaca acgacctcaa     240
agtagaaggg aagagagaga gcaagagcaa gagcagggtt ctccctcata cccacgcagg     300
cagagtggtt atgagaggag acaataccat gagaggagtg agcagaggga agagagagag     360
caagaacaac aacaaggttc tccctcatac tcacgtagac aaaggaaccc ttatcacttc     420
agctctcaaa gattccaaac tctttacaaa aataggaatg gcaaaatccg tgtgctcgag     480
aggtttgacc aaagaaccaa tagacttgag aatctccaaa actaccgcat tgttgagttc     540
caatcaaaac ctaacactct cattctccct aaacactctg atgctgacta cgtcctcgtt     600
gtactcaatg gtagagccac aatcacgata gtaaaccctg atagaagaca agcatataac     660
cttgagtatg gcgatgctct cagaatccca gctggctcaa cttcatatat ccttaacccg     720
gatgacaacc agaagcttag agtagtcaag ctcgcaatac ccatcaacaa tcctggctac     780
ttttatgatt tctatccatc gagtactaaa gaccaacaat cctacttcag tggcttcagc     840
aggaacactt tagaggccac cttcaatact cgttatgaag agatacaaag gattatttta     900
gggaatgagg atgagcaaga atatgaggaa caaggcgtg ggcaagagca gagcgaccaa     960
gacgaggggg tgatagtgat agtttcaaag aaacagatcc aaaaattgac aaaacacgct    1020
caatcttcat caggaaaaga caaaccctct gattctggcc ccttcaactt gagaagcaat    1080
gagcccatat attcaaacaa gtatgggaac ttctatgaaa tcactccaga tagaaaccct    1140
caagttcagg atttgaatat ctctctcacc tatataaaaa ttaacgaggg agctttgttg    1200
ttgccacact ataactcaaa ggccatatat gtagtcgtgg ttgatgaagg agaaggaaat    1260
tatgaactgg taggtattcg agatcaacaa cgacaacaag atgagcaaga agagaaagag    1320
gaagaagtga taaggtatag tgctagatta tcagaaggtg acattttgt aattccagca    1380 ggttatccaa tttccatcaa tgcttcctca aatcttcgct tgcttggatt tggcatcaat    1440
gctgatgaaa accagaggaa tttcctcgca ggttctaaag acaatgtgat aaggcagtta    1500
```

```
gatagagcag tgaatgagct cacattccct ggttctgctg aagatattga gagattaatc    1560
aaaaaccaac aacagtctta ctttgcaaat ggtcagcctc aacaacaaca acaacaacaa    1620
agtgagaagg agggaaggcg tggaagaagg ggttcatctc ttccattttg agcactttt     1680 actaagctgt tttaaaagct actatcatgt aagagctcat agtgagctac tgagagaata    1740
ataaaactaa agttggacct ttgtactaat aatgttaata aaaaaaaaa a              1791
```

```
<210> SEQ ID NO 2
<211> LENGTH: 533
<212> TYPE: PRT
<213> ORGANISM: Lupinus albus

<400> SEQUENCE: 2

Met Gly Lys Met Arg Val Arg Phe Pro Thr Leu Val Leu Val Leu Gly
1               5                   10                  15

Ile Val Phe Leu Met Ala Val Ser Ile Gly Ile Ala Tyr Gly Glu Lys
            20                  25                  30

Asp Val Leu Lys Ser His Glu Arg Pro Glu Glu Arg Glu Gln Glu Glu
        35                  40                  45

Trp Gln Pro Arg Arg Gln Arg Pro Gln Ser Arg Arg Glu Glu Arg Glu
    50                  55                  60

Gln Glu Gln Glu Gln Gly Ser Pro Ser Tyr Pro Arg Arg Gln Ser Gly
65                  70                  75                  80

Tyr Glu Arg Arg Gln Tyr His Glu Arg Ser Glu Gln Arg Glu Glu Arg
                85                  90                  95

Glu Gln Glu Gln Gln Gln Gly Ser Pro Ser Tyr Ser Arg Arg Gln Arg
            100                 105                 110

Asn Pro Tyr His Phe Ser Ser Gln Arg Phe Gln Thr Leu Tyr Lys Asn
        115                 120                 125

Arg Asn Gly Lys Ile Arg Val Leu Glu Arg Phe Asp Gln Arg Thr Asn
130                 135                 140

Arg Leu Glu Asn Leu Gln Asn Tyr Arg Ile Val Glu Phe Gln Ser Lys
145                 150                 155                 160

Pro Asn Thr Leu Ile Leu Pro Lys His Ser Asp Ala Asp Tyr Val Leu
                165                 170                 175

Val Val Leu Asn Gly Arg Ala Thr Ile Thr Ile Val Asn Pro Asp Arg
            180                 185                 190

Arg Gln Ala Tyr Asn Leu Glu Tyr Gly Asp Ala Leu Arg Ile Pro Ala
        195                 200                 205

Gly Ser Thr Ser Tyr Ile Leu Asn Pro Asp Asp Asn Gln Lys Leu Arg
    210                 215                 220

Val Val Lys Leu Ala Ile Pro Ile Asn Asn Pro Gly Tyr Phe Tyr Asp
225                 230                 235                 240

Phe Tyr Pro Ser Ser Thr Lys Asp Gln Gln Ser Tyr Phe Ser Gly Phe
                245                 250                 255

Ser Arg Asn Thr Leu Glu Ala Thr Phe Asn Thr Arg Tyr Glu Glu Ile
            260                 265                 270

Gln Arg Ile Ile Leu Gly Asn Glu Asp Glu Gln Glu Tyr Glu Glu Gln
        275                 280                 285

Arg Arg Gly Gln Glu Gln Ser Asp Gln Asp Glu Gly Val Ile Val Ile
    290                 295                 300

Val Ser Lys Lys Gln Ile Gln Lys Leu Thr Lys His Ala Gln Ser Ser
305                 310                 315                 320
```

```
Ser Gly Lys Asp Lys Pro Ser Asp Ser Gly Pro Phe Asn Leu Arg Ser
            325                 330                 335

Asn Glu Pro Ile Tyr Ser Asn Lys Tyr Gly Asn Phe Tyr Glu Ile Thr
        340                 345                 350

Pro Asp Arg Asn Pro Gln Val Gln Asp Leu Asn Ile Ser Leu Thr Tyr
        355                 360                 365

Ile Lys Ile Asn Glu Gly Ala Leu Leu Pro His Tyr Asn Ser Lys
        370                 375                 380

Ala Ile Tyr Val Val Val Asp Glu Gly Asn Tyr Glu Leu
385                 390                 395                 400

Val Gly Ile Arg Asp Gln Gln Arg Gln Gln Asp Glu Gln Glu Lys
                405                 410                 415

Glu Glu Glu Val Ile Arg Tyr Ser Ala Arg Leu Ser Glu Gly Asp Ile
                420                 425                 430

Phe Val Ile Pro Ala Gly Tyr Pro Ile Ser Ile Asn Ala Ser Ser Asn
                435                 440                 445

Leu Arg Leu Leu Gly Phe Gly Ile Asn Ala Asp Glu Asn Gln Arg Asn
    450                 455                 460

Phe Leu Ala Gly Ser Lys Asp Asn Val Ile Arg Gln Leu Asp Arg Ala
465                 470                 475                 480

Val Asn Glu Leu Thr Phe Pro Gly Ser Ala Glu Asp Ile Glu Arg Leu
                485                 490                 495

Ile Lys Asn Gln Gln Ser Tyr Phe Ala Asn Gly Gln Pro Gln Gln
            500                 505                 510

Gln Gln Gln Gln Gln Ser Glu Lys Glu Gly Arg Gly Arg Arg Gly
        515                 520                 525

Ser Ser Leu Pro Phe
    530

<210> SEQ ID NO 3
<211> LENGTH: 519
<212> TYPE: DNA
<213> ORGANISM: Lupinus albus

<400> SEQUENCE: 3
cgtagacaaa ggaaccctta tcacttcagc tctcaaagat tccaaactct ttacaaaaat      60
aggaatggca aaatccgtgt gctcgagagg tttgaccaaa gaaccaatag acttgagaat     120
ctccaaaact accgcattgt tgagttccaa tcaaaaccta cactctcat tctccctaaa      180 cactctgatg ctgactacgt cctcgttgta ctcaatggta gagccacaat cacgatagta     240
aaccctgata gaagacaagc atataacctt gagtatggcg atgctctcag aatcccagct     300
ggctcaactt catatatcct taacccggat gacaaccaga gcttagagt agtcaagctc      360 gcaataccca tcaacaatcc tggctacttt tatgatttct atccatcgag tactaaagac     420
caacaatcct acttcagtgg cttcagcagg aacactttag aggccacctt caatactcgt     480
tatgaagaga tacaaaggat tattttaggg aatgaggat                            519

<210> SEQ ID NO 4
<211> LENGTH: 173
<212> TYPE: PRT
<213> ORGANISM: Lupinus albus

<400> SEQUENCE: 4

Arg Arg Gln Arg Asn Pro Tyr His Phe Ser Ser Gln Arg Phe Gln Thr
1               5                   10                  15
```

```
Leu Tyr Lys Asn Arg Asn Gly Lys Ile Arg Val Leu Glu Arg Phe Asp
            20              25              30

Gln Arg Thr Asn Arg Leu Glu Asn Leu Gln Asn Tyr Arg Ile Val Glu
        35              40              45

Phe Gln Ser Lys Pro Asn Thr Leu Ile Leu Pro Lys His Ser Asp Ala
    50              55              60

Asp Tyr Val Leu Val Leu Asn Gly Arg Ala Thr Ile Thr Ile Val
65              70              75              80

Asn Pro Asp Arg Arg Gln Ala Tyr Asn Leu Glu Tyr Gly Asp Ala Leu
            85              90              95

Arg Ile Pro Ala Gly Ser Thr Ser Tyr Ile Leu Asn Pro Asp Asp Asn
            100             105             110

Gln Lys Leu Arg Val Val Lys Leu Ala Ile Pro Ile Asn Asn Pro Gly
        115             120             125

Tyr Phe Tyr Asp Phe Tyr Pro Ser Ser Thr Lys Asp Gln Gln Ser Tyr
    130             135             140

Phe Ser Gly Phe Ser Arg Asn Thr Leu Glu Ala Thr Phe Asn Thr Arg
145             150             155             160

Tyr Glu Glu Ile Gln Arg Ile Ile Leu Gly Asn Glu Asp
            165             170
```